(12) United States Patent
Stephens et al.

(10) Patent No.: US 11,622,774 B2
(45) Date of Patent: Apr. 11, 2023

(54) SYSTEMS AND METHODS FOR A HARNESS ATTACHMENT HOOK

(71) Applicant: ARMR Systems LLC, Snellville, GA (US)

(72) Inventors: Andrew James Stephens, Frederick, MD (US); Chibueze Joseph Ihenacho, Wheaton, MD (US)

(73) Assignee: ARMR Systems LLC, Snellville, GA (US)

( * ) Notice: Subject to any disclaimer, the term of this patent is extended or adjusted under 35 U.S.C. 154(b) by 533 days.

(21) Appl. No.: 16/808,171

(22) Filed: Mar. 3, 2020

(65) Prior Publication Data
US 2021/0275190 A1    Sep. 9, 2021

(51) Int. Cl.
*A61B 17/132*    (2006.01)
*A61B 17/00*    (2006.01)

(52) U.S. Cl.
CPC ............... *A61B 17/1325* (2013.01); *A61B 2017/00407* (2013.01); *A61B 2017/00477* (2013.01); *A61B 2017/00862* (2013.01)

(58) Field of Classification Search
CPC .............. A61B 17/132; A61B 17/1322; A61B 17/1325; A61B 17/1327; A61B 17/135; A61B 17/1355; A61B 35/0006; A61B 35/0012; A61B 35/0018; A61B 35/0025; A61B 35/0031; A61B 35/0037; A44B 11/006; A44B 11/008; A44B 11/02; A44B 11/04; A62B 35/0006; A62B 35/0012; A62B 35/0018; A62B 35/0025; A62B 35/0031; A62B 35/0037
See application file for complete search history.

(56) References Cited

U.S. PATENT DOCUMENTS

| | | | | |
|---|---|---|---|---|
| 779,279 | A * | 1/1905 | Hastings | A44B 11/04 24/321 |
| 1,860,170 | A * | 5/1932 | Bronson | A44B 11/04 24/198 |
| 5,295,996 | A * | 3/1994 | Blair | A61B 17/1325 128/119.1 |
| 7,299,527 | B1 * | 11/2007 | Gyure | A44B 11/006 24/265 AL |
| 2005/0066484 | A1 * | 3/2005 | Hum | A44B 11/04 24/321 |

(Continued)

*Primary Examiner* — Kathleen S Holwerda
(74) *Attorney, Agent, or Firm* — Foley & Lardner LLP

(57) ABSTRACT

Described embodiments provide systems and methods for an attachment mechanism for attaching a strap around a body extremity. The attachment mechanism includes a hook, a first channel, and a second channel. The hook includes a first longitudinal axis and coupled to the strap at a first region of the hook. The first channel allowing the attachment mechanism to receive the strap. The second channel extending from the first channel and having an opening allowing the attachment mechanism to secure the strap, the opening extending along a second longitudinal axis, the second longitudinal axis forming an angle of less than ninety degrees with the first longitudinal axis. The strap is coupled to a harness. The strap includes a first portion, an attachment portion attached to the first portion, a main portion attached to the attachment portion; and an elastic portion attached to the main portion.

11 Claims, 22 Drawing Sheets

(56) References Cited

U.S. PATENT DOCUMENTS

| | | | |
|---|---|---|---|
| 2011/0072545 A1* | 3/2011 | Bennett | A41D 13/0543 2/229 |
| 2011/0126382 A1* | 6/2011 | Kirkham | F16G 11/103 24/115 J |
| 2016/0135575 A1* | 5/2016 | Solomon | A45F 5/02 224/235 |
| 2018/0343982 A1* | 12/2018 | Chang | A44B 11/02 |

* cited by examiner

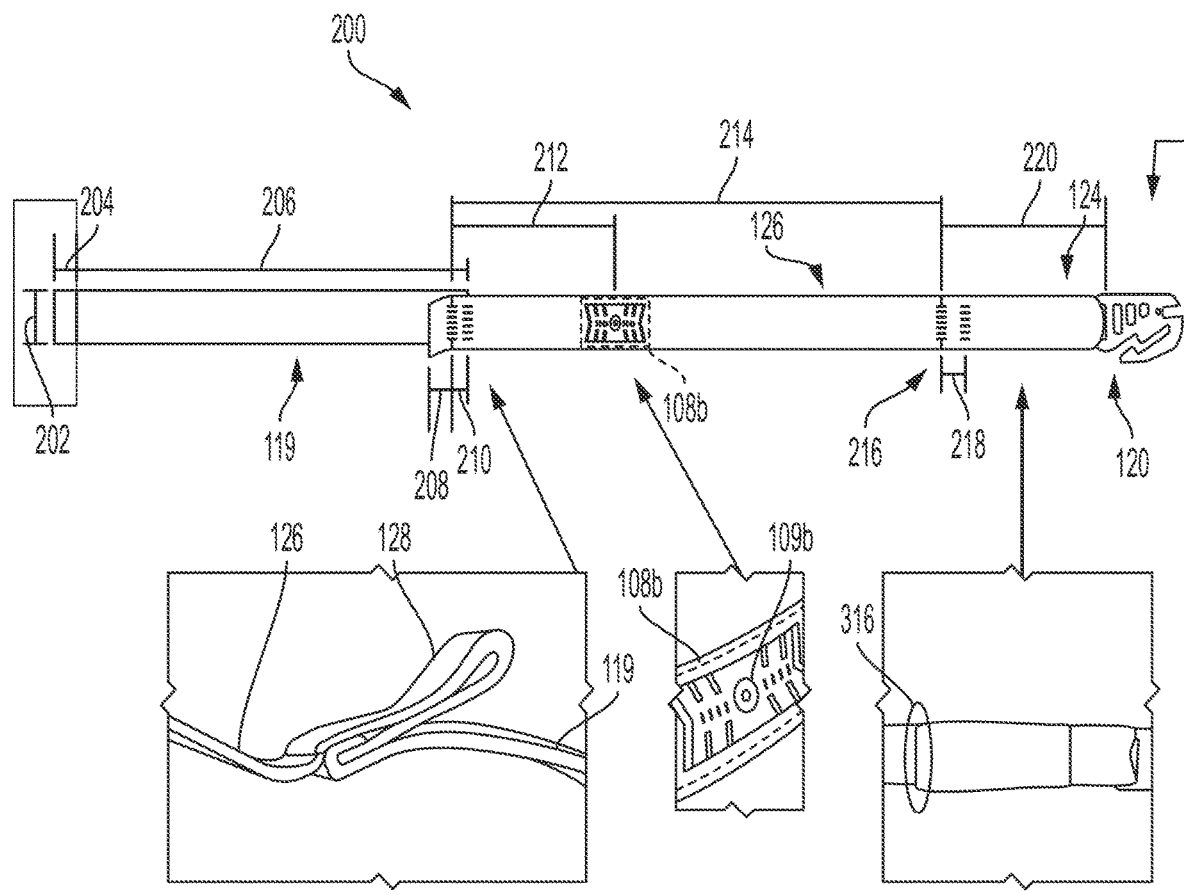
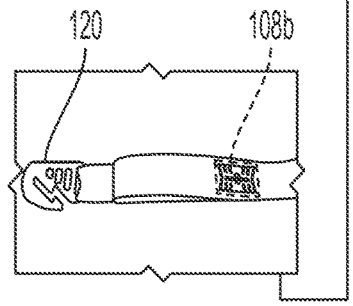

SYSTEMS AND METHODS FOR A HARNESS ATTACHMENT HOOK

FIELD OF THE INVENTION

The present invention relates to a novel way to control trauma wounds.

BACKGROUND

A tourniquet may be used to stop or reduce bleeding that may occur as the result of an injury. The tourniquet may be used to control venous and arterial circulation to the site of the injury. The tourniquet may control the blood flow by applying pressure to the tissue underlying the tourniquet. The applied pressure may occlude the vessels, and prevent or reduce flow there through. However, tourniquets are difficult to obtain and deploy during the traumatic moments associated with an injury.

SUMMARY

A harness attachment hook system may be used to secure a strap to assist with the deployment of a junctional tourniquet. Junctional tourniquets are devices that attempt to treat arterial hemorrhage through the use of direct pressure on the arteries at the junctional areas of the extremities. The tightening combined with the system's pressure profile provides pressure to the artery and limit blood loss. In the event of a traumatic injury, the harness attachment hook system may be used to stop bleeding long enough for the injured person to get access to proper medical attention. The harness attachment hook system may integrate with vests and body armor, in which it may be retracted until it is needed. The harness attachment hook system may then be deployed from the harness and wrapped around the junction point. The strap is secured around the junction point with an attachment hook. The harness attachment hook system may include a fastener and leverage point for the attachment hook.

According to one aspect, an attachment mechanism system for attaching a strap around a body extremity is described. The attachment mechanism includes a hook having a first longitudinal axis and coupled to the strap at a first region of the hook. A first channel allows the attachment mechanism to receive the strap. A second channel extends from the first channel and has an opening allowing the attachment mechanism to secure the strap. The opening extends along a second longitudinal axis. The second longitudinal axis forms an angle of less than ninety degrees with the first longitudinal axis.

In some implementations, the second channel includes grooves to secure the strap. In some implementations, the angle formed by the second longitudinal axis is less than twenty degrees with the first longitudinal axis. In some implementations, a cord is attached at a third region of the hook. In certain implementations, a fastener is attached to the cord. In certain implementations, a mount is engaged to the fastener. In certain implementations, the mount is a Modular Lightweight Load-carrying Equipment (MOLLE) T mount.

In some implementations, a third channel is between the first channel and the second channel. The third channel has a first slit with a first area for gripping the attachment mechanism. In certain implementations, the third channel includes a second slit with a second area and a third slit with a third area. The third area is less than the second area, and the second area is less than the first area.

In another aspect, a system for a tourniquet for controlling blood flow is described. The system includes a strap coupled to a harness. A hook has a first longitudinal axis and is coupled to the strap at a first region of the hook. A first channel is for receiving the strap. A second channel extends from the first channel and has an opening to secure the strap. The opening extends along a second longitudinal axis. The second longitudinal axis forms an angle of less than ninety degrees with the first longitudinal axis.

In some implementations, the strap includes a first portion. An attachment portion is attached to the first portion. A main portion is attached to the attachment portion. An elastic portion is attached to the main portion. In some implementations, the strap includes a hook-fastener disposed between the attachment portion and the main portion. In certain implementations, the first channel is capable of receiving the hook-fastener of the strap.

In some implementations, the main portion includes a rivet for receiving a pressure ratchet. In some implementations, the attachment portion has a first elasticity. In some implementations, the elastic portion has a second elasticity.

In another aspect, a method for attaching a strap around a body extremity for controlling blow flow is described. The method includes providing an apparatus having a hook having a first longitudinal axis and coupled to the strap at a first region of the hook. A first channel is for receiving the strap. A second channel extends from the first channel and has an opening to secure the strap. The opening extends along a second longitudinal axis. The second longitudinal axis forms an angle of less than ninety degrees with the first longitudinal axis. The strap wraps around a junction. The second channel receives the strap to secure the strap around the junction.

In some implementations, providing the apparatus further includes providing a cord attached to a third region of the hook, a fastener attached to the cord; and a mount engaged to the fastener. In certain implementations, the fastener disconnects the mount responsive to wrapping the strap around the junction.

In certain implementations, the cord extends responsive to wrapping the strap around the junction.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 2A illustrates a leg strap and a hook.

FIG. 2B illustrates an enlarged view of the leg strap including the hook fastener.

FIG. 2C illustrates an enlarged view of the leg strap including the guidance point and the compression device fastener.

FIG. 2D illustrates an enlarged view of the elastic portion including the main-elastic portion fastener.

FIG. 2E illustrates an enlarged view of the leg strap including added material.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

In some implementations, the systems and methods described herein are configured to enable fast and reliable hemorrhage control in the extremities. These systems targets to control key arteries serving the extremities. In the case of injury, the strap is deployed from the harness, secured by the attachment hook, and a compression device is applied to a guidance point closest to the injury. Once inserted, the compression device should be tightened to stop the flow of blood. Bleeding may be controlled at multiple sites simultaneously.

Figure 1A:
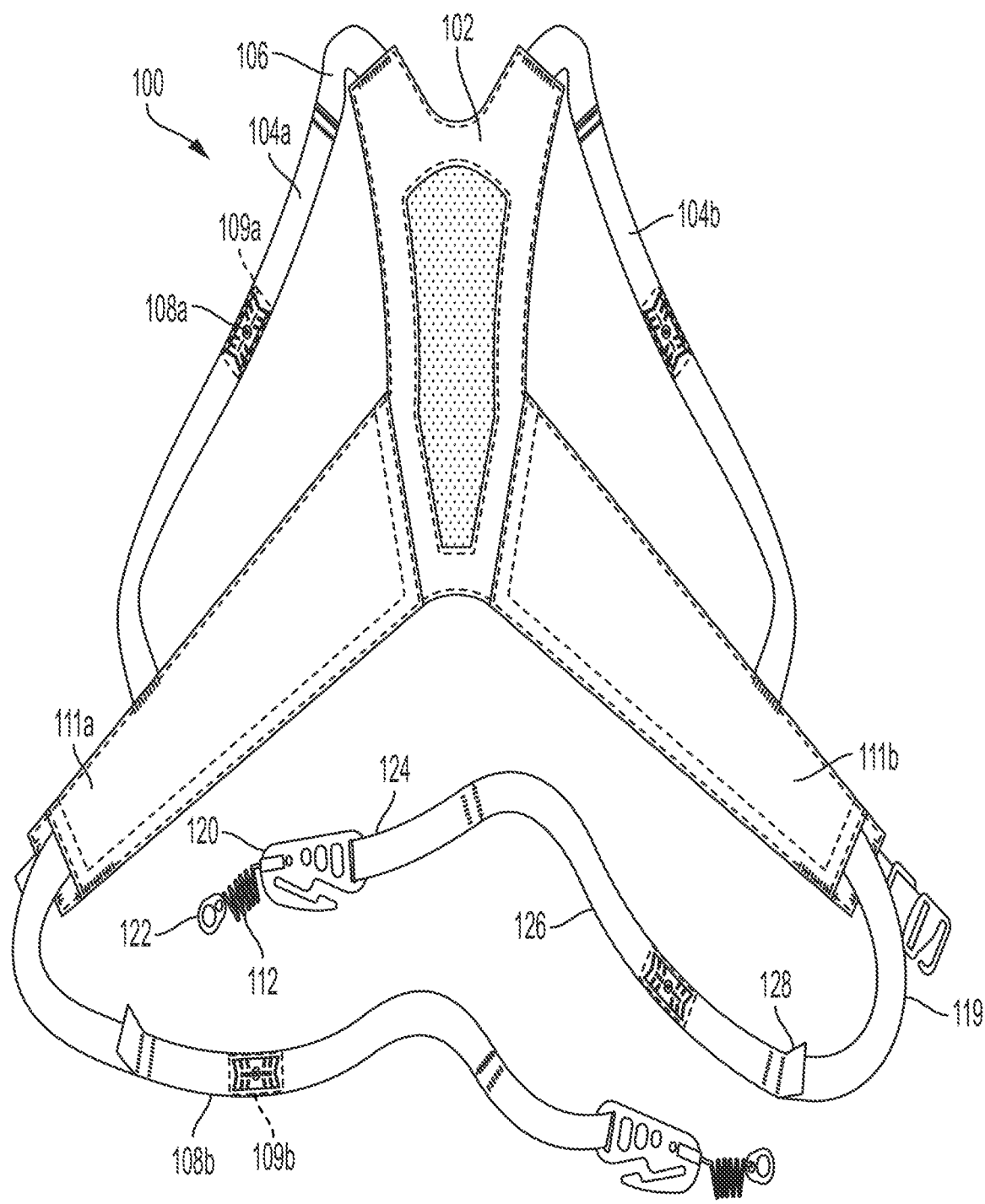
FIG. 1A illustrates a front view of the system for hemorrhage control.

Referring now to FIG. 1A, and in brief overview, illustrated is a front view of the front of the system 100. The system 100 may be worn by a user prior to the use of the system 100, and the front view faces away from the user. The system 100 may include a harness body 102, an arm strap 104a and arm strap 104b (generally referred to as arm strap 104), an arm elastic 106, a guidance point 108a and a guidance point 108b (generally referred to as guidance point 108), a compression device fastener 109a and a compression device fastener 109b (generally referred to as compression device fastener 109), a chest pocket 111a and a chest pocket 111b (generally referred to as chest pocket 111), a coil 112, an attachment portion 119, a hook 120, a coil fastener 122, an elastic portion 124, a main portion 126, and a hook fastener 128. The system 100 may be worn by a user prior to the use of the system 100, and the alternate front view may be worn around both an upper junction area and a lower junction area.

Still referring to FIG. 1A, and in further detail, the system 100 may be light weight. For example, the system 100 may include lightweight materials, such as hard plastics. The harness body 102 may be manufactured from cloth, cotton, polyester, a nylon webbing, polypropylene, or a similar fabric. In some implementations, the harness body 102 may include pockets or pouches constructed from a rip-stop fabric, such as rip-stop nylon fabric. The pockets or pouches may be used to store the components of the system 100 when not in use. The various components of the harness body 102 may be sewn together with threads containing, nylon, cotton, polyester, viscose, rayon, or a combination thereof. In some implementations, the harness body 102 is constructed to meet military specifications. The harness body 102 may include a mesh. The system 100 may also include the arm strap 104 coupled to the harness body 102. The arm strap 104 may be disposed over an upper junction area of the user. The arm strap 104 coupling to the harness body 102 may increase mobility for the user. Part of the arm strap 104 may be inside the harness body 102. The arm strap 104 may be secured or coupled using a harness body arm strap fastener. The harness body arm strap fastener may be a bartack stitch applied on arm strap 104 and harness body 102. The bartack stitch may be applied to the edge of the harness body 102. The arm strap 104 may be constructed out of rubber, cloth, polyester, or cotton.

Still referring to FIG. 1A, the arm strap 104a may include the arm elastic 106 and the guidance point 108a. The arm elastic 106 may stretch up to twice its original distance. In some implementations, the arm elastic 106 may stretch up to three times its original distance. The arm strap 104 may stretch up to twice its original distance. In some implementations, the arm strap 104 may stretch up to three times its original distance. In some implementations, the arm strap 104 may have a different elasticity than arm elastic 106. The guidance point 108 may have a different color than the arm strap 104. The guidance point 108 may apply pressure to the wearer's upper junctional area or lower junctional area. The guidance point 108 may be a circular, square, rectangular, or any other shape that may distribute pressure to the arteries to substantially constrict the flow of blood through the arteries. The corners of the guidance point 108 may be rounded to reduce the chance of injuring the wearer when the guidance point 108 is compressed into the junctional area of the wearer. The guidance point 108 may include identifying information about a compatible compression device, an indicator label, or directions. The guidance point 108 may be stitched or printed into the arm strap 104. The guidance point 108 may be manufactured out of reflective material or glow in the dark material. The guidance point 108 may include arrows pointing towards the fastener for the compression device. The guidance point 108 may have three sets of lines on each side of the fastener for the compression device. The lines may be of a reflective color. The lines may be a different color than the fastener for the compression device. The lines may be a different color than the rest of the guidance point 108. The lines may be manufactured to glow in the dark.

Still referring to FIG. 1A, the guidance point 108*a* may include the compression device fastener 109*a*. The compression device (not pictured) may couple to the compression device fastener 109 at any of the wearer's junctional areas. The guidance point 108 and compression device fastener 109 allow for the application of the compression device (not pictured) to apply pressure to control the tourniquet.

Still referring to FIG. 1A, the system 100 may also include an attachment portion 119. The attachment portion 119 may be manufactured from adhesive material. The attachment portion 119 may be inelastic. The attachment portion 119 couples to the hook 120. The hook 120 is coupled to a coil fastener 122 and an elastic portion 124. The coil fastener 122 may be manufactured out of metal. In some implementations, the coil fastener 122 is a snap applicator. The coil fastener 122 may be adhesive, tape, glue, a zipper, snaps, laces, or a hook-and-loop fastener. The elastic portion 124 may stretch up to twice its original distance. In some implementations, the elastic portion 124 may stretch up to three times its original distance. The elastic portion 124 is coupled to the main portion 126. The attachment portion 119 and the main portion 126 are coupled to the hook fastener 128. The hook fastener 128 may secure the hook 120 to the attachment portion 119. The hook fastener 128 may be a snag tab. The hook fastener 128 may be a portion of the main portion 126 extending over the attachment portion 119. The attachment portion 119, the main portion 126, or the elastic portion 124 may be disposed inside the chest pocket 111 of the system 100. The attachment portion 119, the main portion 126, or the elastic portion 124 may be pulled outside of the chest pocket 111. If the attachment portion 119, the main portion 126, or the elastic portion 124 are not pulled, then they may automatically recede back into the chest pocket 111. The arm strap 104 may be connected to the edge of the chest pocket 111. The arm strap 104 coupling to the chest pocket 111 may increase mobility for the user. Part of the arm strap 104 may be inside the chest pocket 111. The arm strap 104 may extend into the chest pocket 111. The chest pocket arm strap fastener may secure or couple the arm strap 104 to the chest pocket 111 by using a bartack stitch applied on arm strap 104 and chest pocket 111. The bartack stitch may be applied to the edge of the chest pocket 111.

Figure 1B:
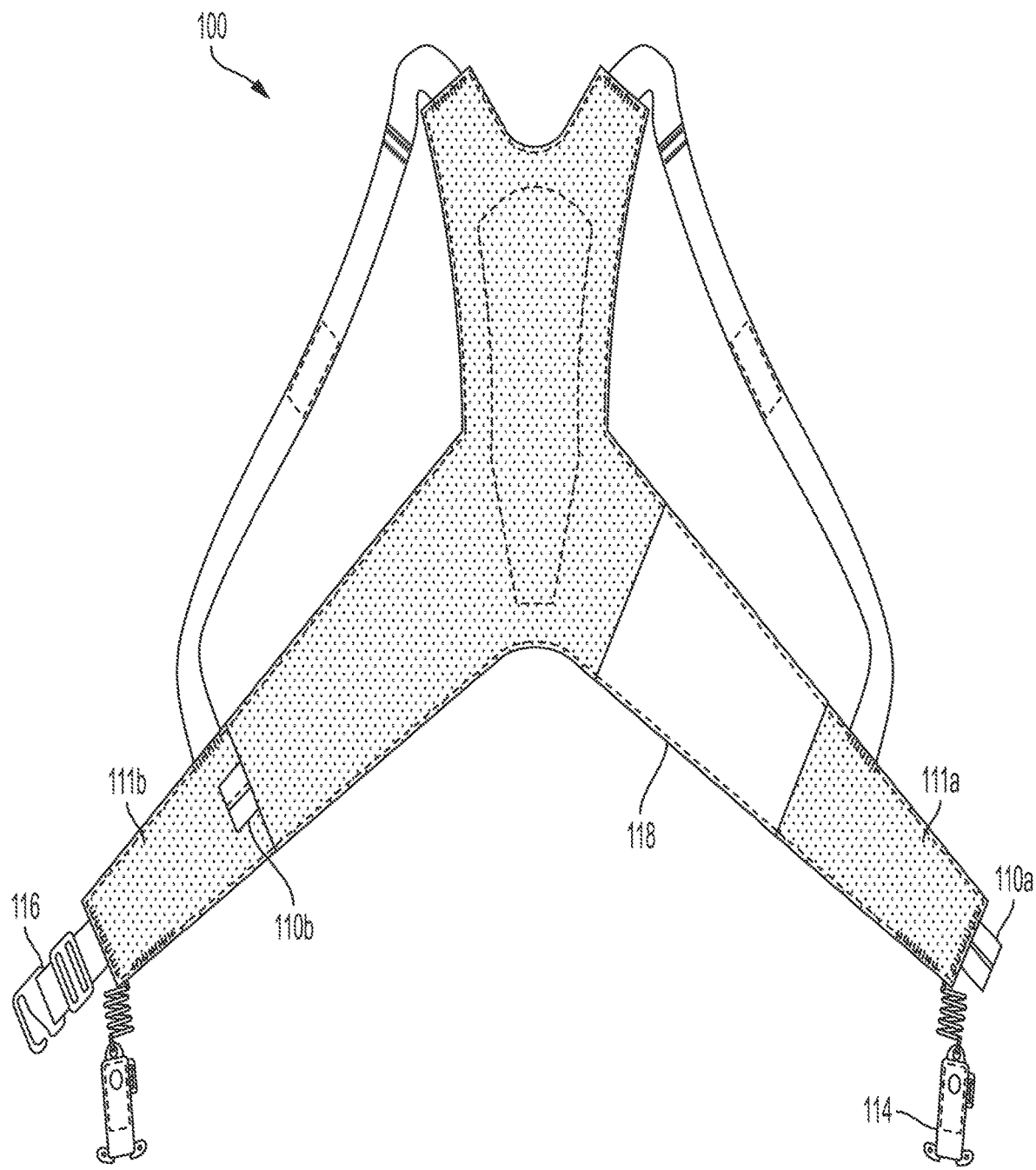
FIG. 1B illustrates a rear view of the system.

Referring now to FIG. 1B, and in brief overview, illustrated is a rear view of the system 100. The system 100 may include a chest strap fastener 110, a mount 114, a chest strap 116, a label 118, and a chest strap fastener 110*b*. The system 100 may be worn by a user prior to the use of the system 100, and the rear view faces towards the user.

Still referring to FIG. 1B, and in further detail, the system 100 may also include the chest strap 116 coupled to the system 100. The chest strap 116 may be disposed inside the chest pocket 111 of the system 100. The chest strap 116 may pull out of the chest pocket 111*b*. If the chest strap 116 is not pulled, then the chest strap 116 may automatically recede back into the chest pocket 111*b*. A chest strap fastener 110*a* is disposed inside the chest pocket 111 of the harness body 102. The chest strap fastener 110*a* may pull out of the chest pocket 111*a*. If the chest strap fastener 110*a* is not pulled, then it may automatically recede back into the chest pocket 111*a*. The chest strap 116 may couple with the chest strap fastener 110*a*. The chest strap 116 may couple with the chest strap fastener 110*a* may form a continuous strap. The system 100 is coupled to the coil 112. The coil 112 may stretch up to twice its original distance. In some implementations, the coil 112 may stretch up to three times its original distance. The coil 112 is coupled to a mount 114. In some implementations, the mount 114 may couple to a modular lightweight load-carrying equipment (MOLLE) loop. The mount 114 may be adhesive, tape, glue, a zipper, snaps, laces, or a hook-and-loop fastener.

Still referring to FIG. 1B, the system 100 may include a label 118. The label 118 may include identifying information about the user, instructions of use, manufacturer information, model number, serial number, or system 100 size. The label 118 may be printed or stitched into the harness body 102. The system 100 may also include a chest strap fastener 110*b*. The chest strap fastener 110*b* is disposed inside the harness body 102. The chest strap fastener 110*b* is pulled from the harness body 102. If the chest strap fastener 110*b* is not pulled, then it automatically recedes back into the harness body 102. The chest strap 116 couples with the chest strap fastener 110*b*. The chest strap 116 coupled with the chest strap fastener 110*b* may form a continuous strap. The chest strap 116 and chest strap fastener 110*b* may enable the wearer to secure and tighten the system 100 about the wearer's abdomen. In some implementations, the system 100 may be quickly removed from the wearer. For example, the plurality of buckles may facilitate medical professionals or others in quickly removing the system 100 during emergency or other situations.

Referring now to FIG. 2A, and in brief overview, illustrated is a leg strap 300 and the hook 120. The leg strap 300 and hook 120 may include a leg strap width 202, a leg strap fastened portion length 204, a first leg strap length 206, a hook fastener length 208, a second leg strap length 210, a third leg strap length 212, a fourth leg strap length 214, a main-elastic portion fastener 216, a fifth leg strap length 218, and a sixth leg strap length 220. The leg strap 300 and the hook 120 may allow the user to secure the system 100 around a lower junctional area or an upper junctional area.

Still referring to FIG. 2A, and in further detail, the leg strap width 202 may be the width of the leg strap 300. The leg strap width 202 may be one inch. In some implementations, the leg strap width 202 is between ⅛ of an inch and five inches. In some implementations, the leg strap width 202 is ¼ inches. In some implementations, the leg strap width 202 is ⅝ inches. In some implementations, the leg strap width 202 is 2 inches. In some implementations, the leg strap width 202 is 3 inches. In some implementations, the leg strap width 202 is 4 inches. The leg strap 300 may have the same leg strap width 202 along its entire length. The leg strap width 202 may equal the width of the arm strap 104.

Still referring to FIG. 2A, the leg strap fastened portion length 204 may include the length of the leg strap 300 coupled to the chest pocket 111. The leg strap fastened portion length 204 may be 0.5 inches. In some implementations, the leg strap fastened portion length 204 is between ⅛ of an inch and five inches. In some implementations, the leg strap fastened portion length 204 is ¼ inches. In some implementations, the leg strap fastened portion length 204 is ⅝ inches. In some implementations, the leg strap fastened portion length 204 is 2 inches. In some implementations, the leg strap fastened portion length 204 is 3 inches. In some implementations, the leg strap fastened portion length 204 is 4 inches.

Still referring to FIG. 2A, the first leg strap length 206 may include the length of the between the attachment portion 119 without including the leg strap fastened portion length 204. The attachment portion 119 may include red webbing. The first leg strap length 206 may be 15.25 inches. In some implementations, the first leg strap length 206 is 16.25 inches. In some implementations, the first leg strap length 206 is 17 inches. In some implementations, the first leg strap length 206 is 18 inches. In some implementations, the first leg strap length 206 is 19 inches.

Still referring to FIG. 2A, the hook fastener length 208 may include the length of the hook fastener 128. The hook fastener length 208 may be 0.75 inches. In some implementations, the hook fastener length 208 is 0.25 inches. In some implementations, the hook fastener length 208 is 0.5 inches. In some implementations, the hook fastener length 208 is 1 inch. In some implementations, the hook fastener length 208 is 1.5 inches.

Still referring to FIG. 2A, the second leg strap length 210 may include the length of the overlap between the main portion 126 and the attachment portion 119. In some implementations, the second leg strap length 210 couples with attachment portion 119 to the main portion 126 with a stitch. In some implementations, the second leg strap length 210 couples with attachment portion 119 to the main portion 126 with a fastener. The second leg strap length 210 may be 0.5 inches. In some implementations, the second leg strap length 210 is 0.25 inches. In some implementations, the second leg strap length 210 is 0.75 inches. In some implementations, the second leg strap length 210 is 1 inch. In some implementations, the second leg strap length 210 is 1.5 inches.

Still referring to FIG. 2A, the third leg strap length 212 may include the length between the hook fastener 128 and the guidance point 108b. The third leg strap length 212 may be 5.75 inches. In some implementations, the third leg strap length 212 is 6 inches. In some implementations, the third leg strap length 212 is 7 inches. In some implementations, the third leg strap length 212 is 7.75 inches. In some implementations, the third leg strap length 212 is 8 inches.

Still referring to FIG. 2A, the fourth leg strap length 214 may include the length between the hook fastener 128 and the elastic portion 124. The fourth leg strap length 214 may include the main portion 126. The main portion 126 may include black webbing. The fourth leg strap length 214 may be 17 inches. In some implementations, the fourth leg strap length 214 is 17.5 inches. In some implementations, the fourth leg strap length 214 is 18 inches. In some implementations, the fourth leg strap length 214 is 18.5 inches. In some implementations, the fourth leg strap length 214 is 19 inches.

Still referring to FIG. 2A, the main-elastic portion fastener 216 may couple the elastic portion 124 to the main portion 126. In some implementations, the main-elastic portion fastener 216 is a stitch. In some implementations, the main-elastic portion fastener 216 is a thread. In some implementations, the main-elastic portion fastener 216 is sewn into the main portion 126 and the elastic portion 124. In some implementations, the main-elastic portion fastener 216 is a set bartack stitches. The bartack stitches may create a smooth transition between the elastic portion 124 and the main portion 126.

Still referring to FIG. 2A, the fifth leg strap length 218 may include the length of the overlap between the main portion 126 and the elastic portion 124. In some implementations, the fifth leg strap length 218 is the length of the main-elastic portion fastener 216. In some implementations, the fifth leg strap length 218 is the distance between two stitches. The fifth leg strap length 218 may be 0.5 inches. In some implementations, the fifth leg strap length 218 is 0.25 inches. In some implementations, the fifth leg strap length 218 is 0.75 inches. In some implementations, the fifth leg strap length 218 is 1 inch. In some implementations, the fifth leg strap length 218 is 1.5 inches.

Still referring to FIG. 2A, the sixth leg strap length 220 may include the length of the elastic portion 124 between the hook 120 and the main portion 126. The sixth leg strap length 220 may be 6.25 inches. In some implementations, the sixth leg strap length 220 is 6.5 inches. In some implementations, the sixth leg strap length 220 is 6.75 inches. In some implementations, the sixth leg strap length 220 is 7 inches. In some implementations, the sixth leg strap length 220 is 7.25 inches.

Referring now to FIG. 2B, and in brief overview, illustrated is an enlarged view of the leg strap 300 including the hook fastener 128. The hook fastener 128 may be adjacent to the attachment portion 119 and the main portion 126. The hook fastener 128 may secure the hook 120.

Still referring to FIG. 2B, and in further detail, the hook fastener 128 may include the main portion 126. The hook fastener 128 may include the main portion 126 disposed over the attachment portion 119. The hook fastener 128 may include a loop for securing the hook 120. The hook fastener 128 may prevent the slipping or sliding of the hook 120 when it is coupled to the attachment portion 119.

Referring now to FIG. 2C, illustrated is an enlarged view of the leg strap 300 including the guidance point 108b and the compression device fastener 109b. The guidance point 108b and the compression device fastener 109b may assist with using the compression device (not pictured) to apply pressure to a junctional area. A plurality of compression devices (not pictured) may be coupled to the system 100 at any one time. For example, one compression device may be applied over to compression device fastener 109a, and a second compression device may be applied to compression device fastener 109b.

Referring now to FIG. 2D, illustrated is an enlarged view of the elastic portion 124 including the main-elastic portion fastener 216. The main-elastic portion fastener 216 may include two bartack stiches for strengthening or securing the main portion 126 to the elastic portion 124.

Referring now to FIG. 2E, illustrated is an enlarged view of the hook 120 and the guidance point 108b. The leg strap 300 may be manufactured such that the hook 120 and the guidance point 108b form a straight length between them. The straight length may include the first leg strap length 206 and the third leg strap length 212.

Figure 2F:
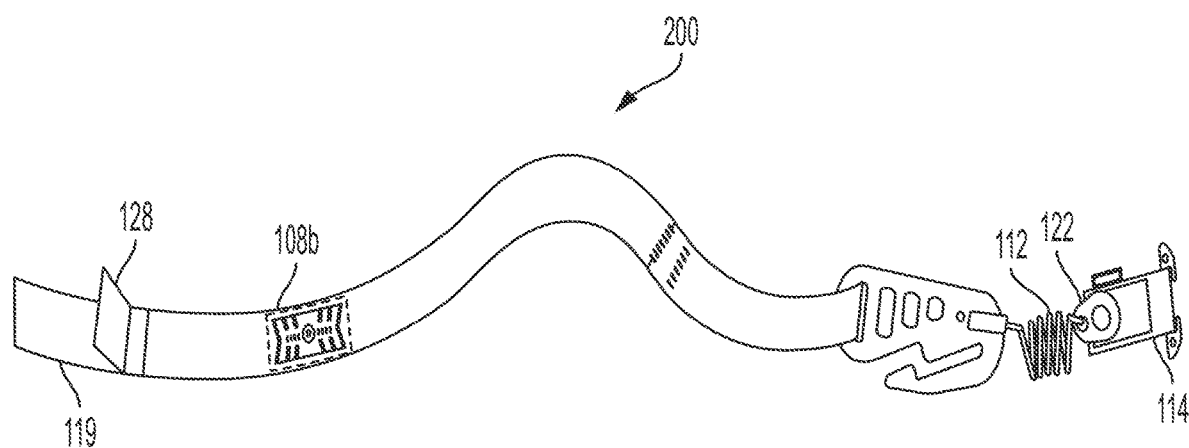
FIG. 2F illustrates the leg strap with the coil and the mount.

Referring now to FIG. 2F, illustrated is an enlarged view of the leg strap 300 with the coil 112, the mount 114, and the coil fastener 122. The coil 112, the mount 114, and the coil fastener 122 may secure the leg strap 300 until it is needed.

Figure 3A:
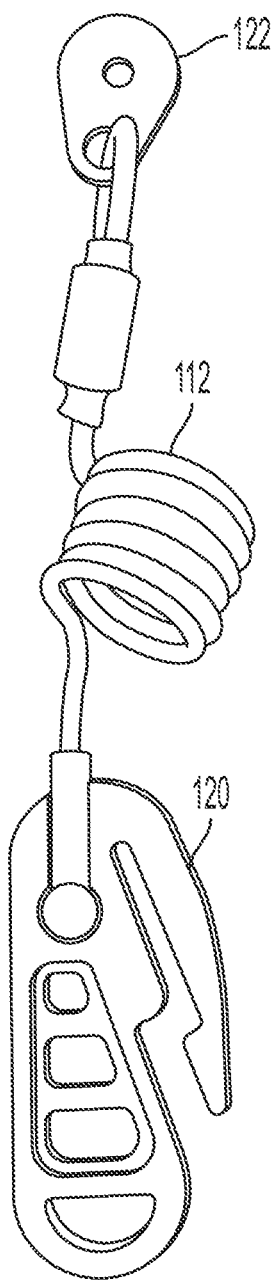
FIG. 3A illustrates the hook, the coil, and the coil fastener.

Referring now to FIG. 3A, illustrated is the hook 120, the coil 112, and the coil fastener 122. The coil 112 may include six loops in a non-stretched state. The coil 112 and the coil fastener 122 may secure the hook 120 until it is needed.

Figure 3B:
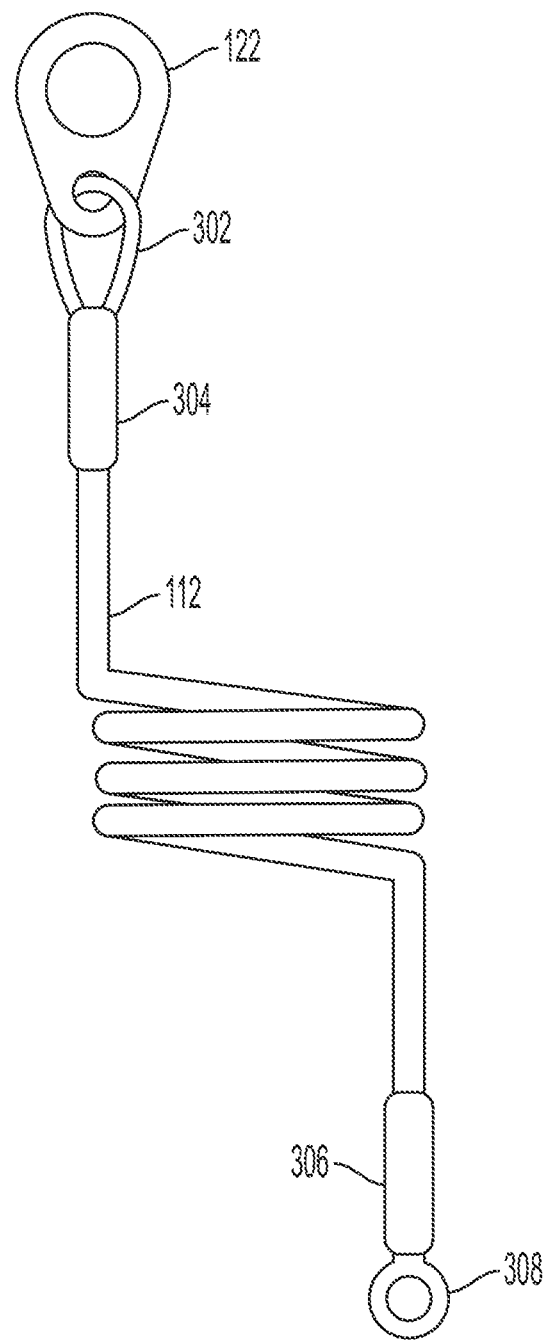
FIG. 3B illustrates an enlarged view of the coil and the coil fastener.

Referring now to FIG. 3B, and in brief overview, illustrated is an enlarged view of the coil 112 and the coil fastener 122. The coil 112 may include a coil-mount fastener 302, a first coil stopper 304, a second coil stopper 306, and a coil-hook fastener 308. The coil 112 may maintain the connection between the hook 120 and the mount 114.

Still referring to FIG. 3B, and in further detail, the coil-mount fastener 302 may include looping the coil 112 into the coil fastener 122. The coil 112 may include four coils. The coil-mount fastener 302 may be secured with the first coil stopper 304. The first coil stopper 304 may be manufactured out of rubber. The coil-hook fastener 308 may attach to the hook 120. The coil-hook fastener 308 may snap into the hook 120, or the coil-hook fastener 308 may be an adhesive to attach to the hook 120. The coil-hook fastener 308 may be secured with the second coil stopper 306. The first coil stopper 304 may be manufactured out of rubber.

Figure 3C:
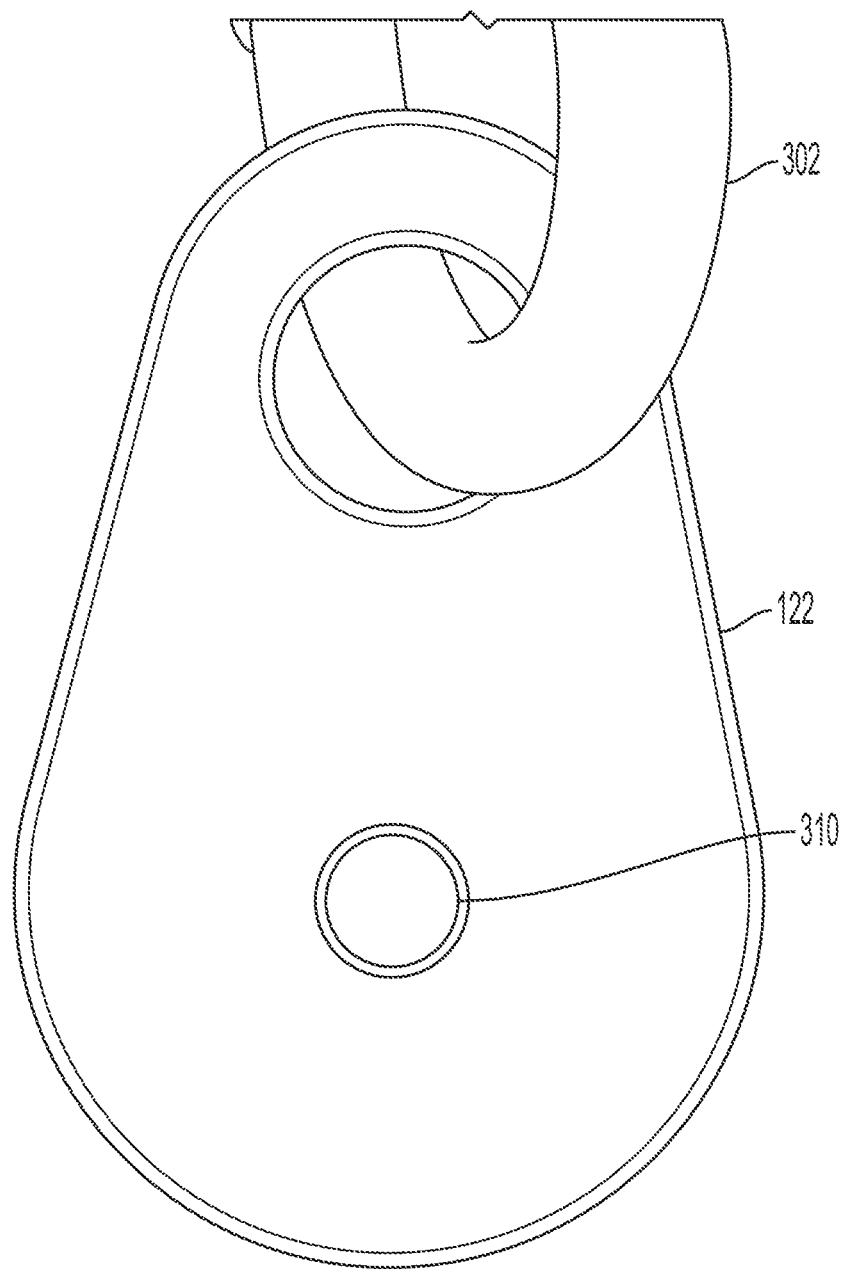
FIG. 3C illustrates an enlarged view of the coil fastener.

Referring now to FIG. 3C, illustrated is an enlarged view of the coil fastener 122. The coil fastener 122 may include the coil fastener snap 310. The mount fastener 408 is coupled to the coil-mount fastener 302. The coil fastener snap 310 may couple to the mount 114.

Figure 4A:
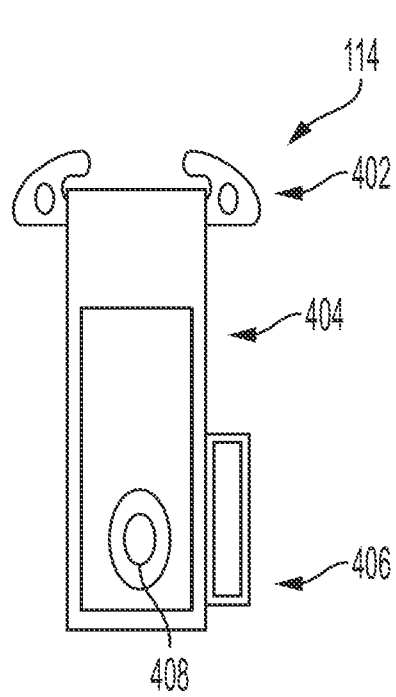
FIG. 4A illustrates a front view of the mount.

Referring now to FIG. 4A, and in brief overview, illustrated is a front view of the mount 114. The mount 114 may include a vest mount 402, a mount webbing 404, a mount label 406, and a mount fastener 408. The mount 114 may attach to piece of clothing to secure the system 100.

Still referring to FIG. 4A, and in further detail, the vest mount 402 may be manufactured from stainless steel, aluminum, titanium, rubber, glass filled nylon, carbon fiber, polyether ether ketone (PEEK), nylon, 3-D printed materials, polyethylene terephthalate (PET), plastic, rubber, lightweight materials, or a combination thereof. The vest mount 402 may be adhesive, tape, glue, a zipper, snaps, laces, or a hook-and-loop fastener. The vest mount 402 may be a plastic "T" mount. The vest mount 402 may couple to the piece of clothing to secure the mount 114. The mount webbing 404 may include the cloth, cotton, polyester, a nylon webbing, polypropylene, or a similar fabric that makes up the structure of the vest mount 402. The mount label 406 may include identifying information about the system 100, mount 114, instructions of use, manufacturer information, model number, serial number, or system size. The mount label 406 may be printed or stitched into the mount 114. The mount fastener 408 may be a large metal snap. The mount fastener 408 may be a male fastener. The mount fastener 408 may couple to the coil fastener 122.

Figure 4B:
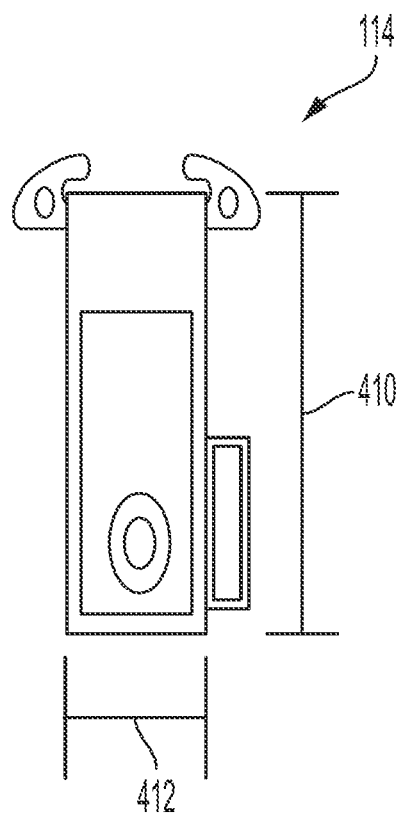
FIG. 4B illustrates an alternate front view of the mount

Referring now to FIG. 4B, and in brief overview, illustrated is an alternate front view of the mount 114. The mount 114 may include a mount length 410 and a mount width 412. The mount length 410 and mount width 412 may make the mount 114 compatible with a variety of clothing items.

Still referring to FIG. 4B, and in further detail, the mount length 410 may be 2 inches. In some implementations, the mount length 410 is 1.5 inches. In some implementations, the mount length 410 is 2.5 inches. In some implementations, the mount length 410 is 1 inch. In some implementations, the mount length 410 is 3 inches.

Still referring to FIG. 4B, the mount width 412 may be 1 inch. In some implementations, the mount width 412 is 1.5 inches. In some implementations, the mount width 412 is 0.5 inches. In some implementations, the mount width 412 is 2 inches. In some implementations, the mount width 412 is 1.25 inches.

Figure 4C:
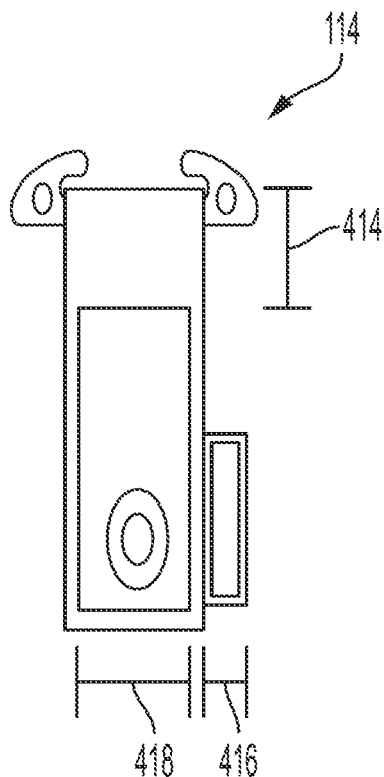
FIG. 4C illustrates an alternate front view of the mount.

Referring now to FIG. 4C, and in brief overview, illustrated is an alternate front view of the mount 114. The mount 114 may include a vest mount buffer length 414, a mount label width 416, and a mount webbing width 418. The vest mount buffer length 414, the mount label width 416, and the mount webbing width 418 may make the mount 114 compatible with a variety of clothing items.

Still referring to FIG. 4C, and in further detail, the vest mount buffer length 414 may represent the distance between the mount webbing 404 and the vest mount 402. The vest mount buffer length 414 may be 0.5 inches. In some implementations, the vest mount buffer length 414 is 0.25 inches. In some implementations, the vest mount buffer length 414 is 0.75 inches. In some implementations, the vest mount buffer length 414 is 1 inch. In some implementations, the vest mount buffer length 414 is 1.25 inches.

Still referring to FIG. 4C, the mount label width 416 may be 0.25 inches. In some implementations, the mount label width 416 is 0.5 inches. In some implementations, the mount label width 416 is 0.2 inches. In some implementations, the mount label width 416 is 0.3 inches. In some implementations, the mount label width 416 is 0.4 inches.

Still referring to FIG. 4C, the mount webbing width 418 may represent the width of the mount webbing 404. The mount webbing width 418 may be 0.75 inches. In some implementations, the mount webbing width 418 is 1 inch. In some implementations, the mount webbing width 418 is 0.5 inches. In some implementations, the mount webbing width 418 is 1.5 inches. In some implementations, the mount webbing width 418 is 1.25 inches.

Figure 4D:
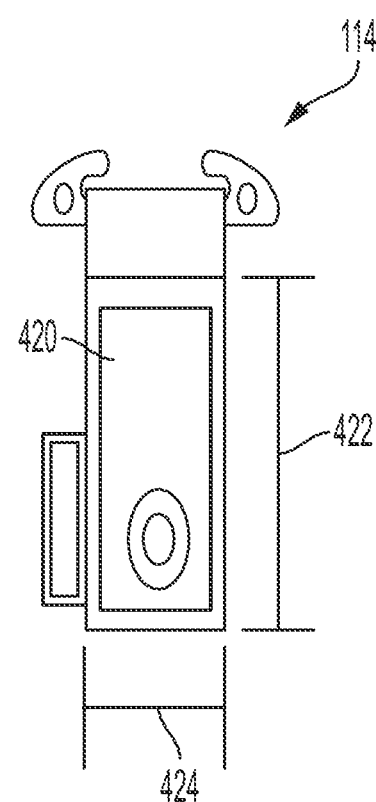
FIG. 4D illustrates a rear view of the mount.

Referring now to FIG. 4D, illustrated is a rear view of the mount 114. The mount 114 may include an internal mount stitching 420, a mount stitching length 422, and a mount stitching width 424. The internal mount stitching 420, the mount stitching length 422, and the mount stitching width 424 may provide structural integrity to the mount 114.

Still referring to FIG. 4D, and in further detail, the internal mount stitching 420 may be sewn together with threads containing, nylon, cotton, polyester, viscose, rayon, or a combination thereof. The internal mount stitching 420 may be sewn together in a rectangular formation.

Still referring to FIG. 4D, the mount stitching length 422 may represent the length of the mount 114 subtracting the vest mount buffer length 414. The mount stitching length 422 may represent the length of the internal mount stitching 420 disposed on the mount 114. The mount stitching length 422 may be 1.5 inches. In some implementations, the mount stitching length 422 is 1.25 inches. In some implementations, the mount stitching length 422 is 1.75 inches. In some implementations, the mount stitching length 422 is 2 inches. In some implementations, the mount stitching length 422 is 2.25 inches.

Still referring to FIG. 4D, the mount stitching width 424 may represent the width of the internal mount stitching 420 disposed on the mount 114. The mount stitching width 424 may equal the mount width 412. The mount stitching width 424 may be 1 inch. In some implementations, the mount stitching width 424 is 1.25 inches. In some implementations, the mount stitching width 424 is 0.75 inches. In some implementations, the mount stitching width 424 is 1.1 inches. In some implementations, the mount stitching width 424 is 0.9 inches.

Figure 5A:
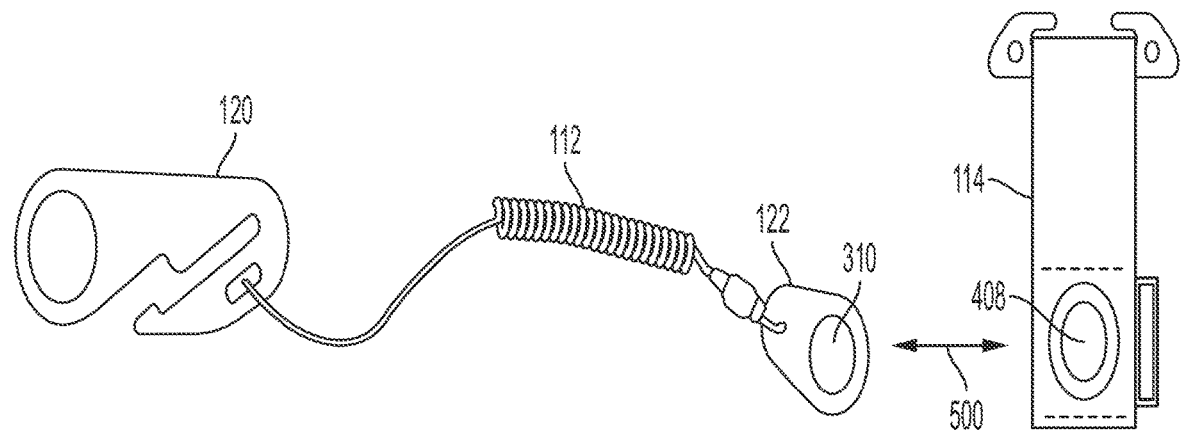
FIG. 5A illustrates the coil coupling to the mount.
Figure 5B:
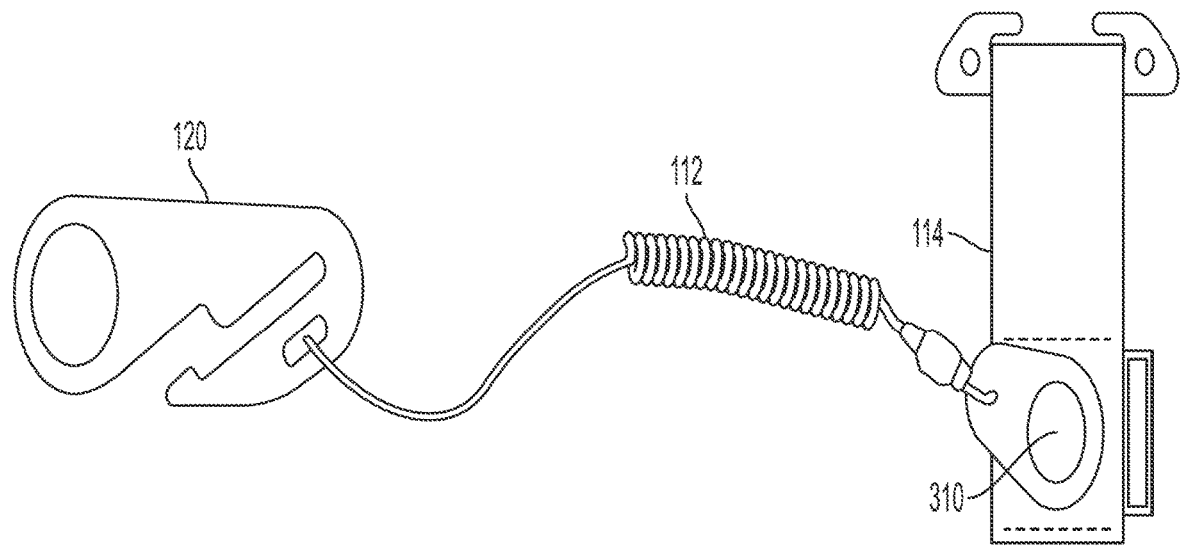
FIG. 5B illustrates the coil coupled to the mount.

Referring now to FIG. 5A, and in brief overview, illustrated is the coil 112 coupling to the mount 114. Attaching the coil 112 to the mount 114 may allow the hook 120 to be securely stowed until it is needed. The coil fastener snap 310 may include a male rivet. The mount fastener 408 may include a female rivet. The step 500 attaches the coil 112 to the mount 114. The step 500 may include the coil fastener snap 310 coupling to the mount fastener 408. The step 500 may include placing the coil fastener snap 310 over the mount fastener 408 and applying pressure. Referring now to FIG. 5B, illustrated is the coil 112 coupled to the mount 114. The mount 114 may secure the hook 120 until it is needed. The coil fastener snap 310 may spin around the mount fastener 408 while still maintaining its connection.

Figure 6:
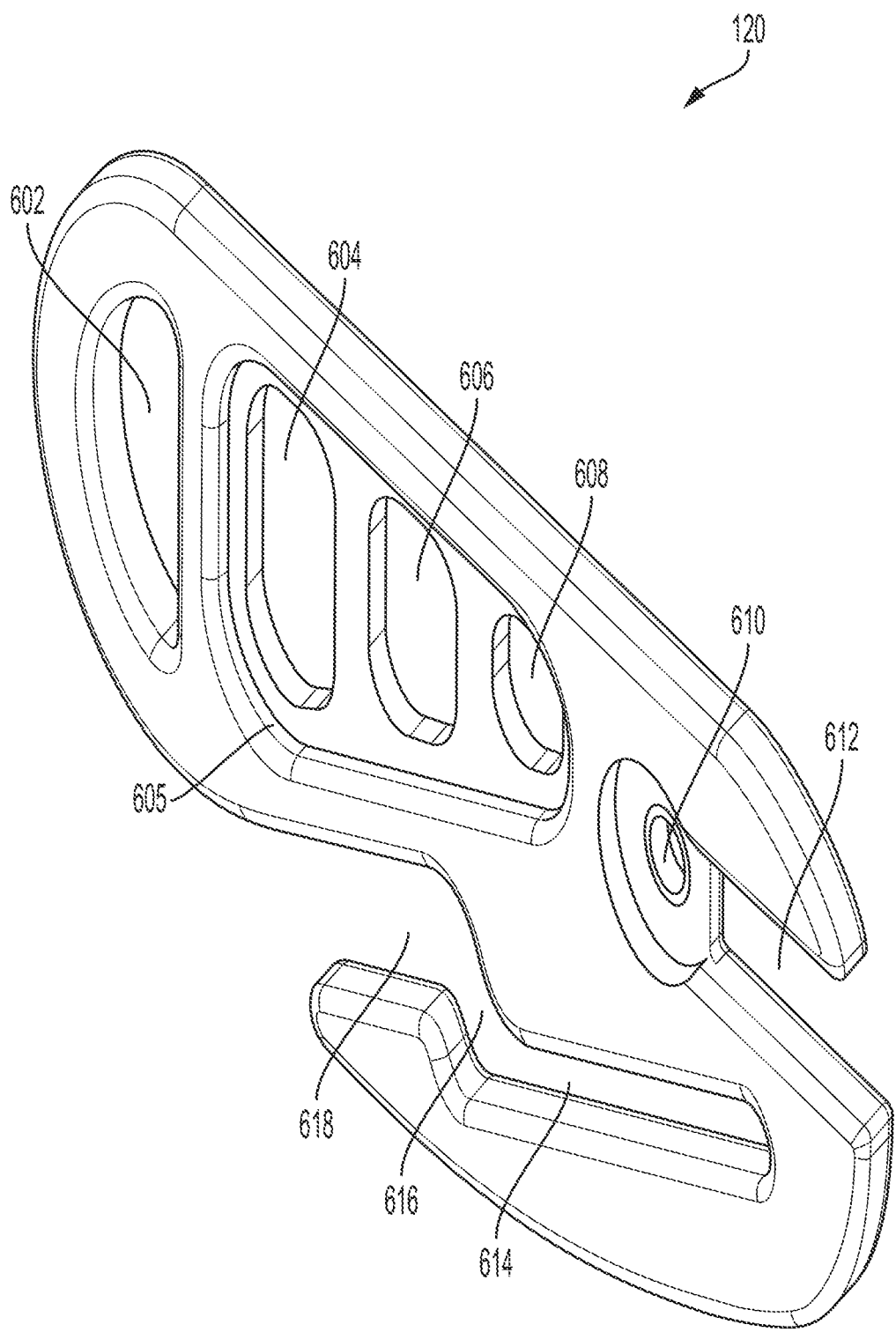
FIG. 6 illustrates a perspective view of the hook.

Referring now to FIG. 6, and in brief overview, illustrated is a perspective view of the hook 120. The hook 120 may include a hook-leg strap fastener 602, a first hook grip 604, hook grip perimeter 605, a second hook grip 606, a third hook grip 608, a hook-coil fastener 610, a hook-coil channel 612, a first leg strap channel 614, a second leg strap channel 616, and a third leg strap channel 618. The hook 120 may provide connection points for two positions on the leg strap 300 and the coil 112.

Still referring to FIG. 6, and in further detail, the hook-leg strap fastener 602 may couple to the leg strap 300. The hook-leg strap fastener 602 may couple to the elastic portion 124 of the leg strap 300. The elastic portion 124 may loop into the hook-leg strap fastener 602. The first hook grip 604 may provide an attachment or grip during operation of the hook 120. In some implementations, the first hook grip 604 couples with the leg strap 300. The second hook grip 606 may provide an attachment or grip during operation of the hook 120. In some implementations, the second hook grip 606 couples with the leg strap 300. The third hook grip 608 may provide an attachment or grip during operation of the hook 120. In some implementations, the third hook grip 608 couples with the leg strap 300. The first hook grip 604, the second hook grip 606, and the third hook grip 608 may be disposed within a hook grip perimeter 605. The hook grip perimeter 605 may be an internal section within the hook 120. The hook grip perimeter 605 may extend around the first hook grip 604, the second hook grip 606, and the third hook grip 608.

Still referring to FIG. 6, the hook-coil fastener 610 may receive the coil-hook fastener 308. The hook-coil fastener 610 may couple to the coil-hook fastener 308. The hook-coil channel 612 may receive the second coil stopper 306. The hook-coil channel 612 may constrict the movement of the second coil stopper 306. The hook-coil channel 612 may be disposed on an edge of the hook 120 opposite the hook-leg strap fastener 602. The hook-coil channel 612 may be parallel to the hook-leg strap fastener 602. The hook 120 may extend along a first longitudinal axis. The hook-coil channel 612 may extend along the first longitudinal axis. The hook-coil channel 612 may extend along a third longitudinal axis, the third longitudinal axis forming an angle of less than ninety degrees with the first longitudinal axis. In some implementations, the third longitudinal axis forms an angle of 5 degrees with the first longitudinal axis. In some implementations, the third longitudinal axis forms an angle of 10 degrees with the first longitudinal axis. In some implementations, the third longitudinal axis forms an angle of 15 degrees with the first longitudinal axis. In some implementations, the third longitudinal axis forms an angle of 20 degrees with the first longitudinal axis. In some implementations, the third longitudinal axis forms an angle of 25 degrees with the first longitudinal axis.

Still referring to FIG. 6, the first leg strap channel 614 may extend along a second longitudinal axis, the second longitudinal axis forming an angle of less than ninety degrees with the first longitudinal axis. In some implementations, the second longitudinal axis forms an angle of 10 degrees with the first longitudinal axis. In some implementations, the second longitudinal axis forms an angle of 20 degrees with the first longitudinal axis. In some implementations, the second longitudinal axis forms an angle of 30 degrees with the first longitudinal axis. In some implementations, the second longitudinal axis forms an angle of 40 degrees with the first longitudinal axis. In some implementations, the second longitudinal axis forms an angle of 50 degrees with the first longitudinal axis. The first leg strap channel 614 may have an opening to secure the leg strap 300. The first leg strap channel 614 may have an opening to secure the attachment portion 119 of the leg strap 300.

Still referring to FIG. 6, the second leg strap channel 616 may extend along a fourth longitudinal axis, the fourth longitudinal axis forming an angle less than 90 degrees with the third longitudinal axis. In some implementations, the fourth longitudinal axis forms an angle of 25 degrees with the third longitudinal axis. In some implementations, the fourth longitudinal axis forms an angle of 35 degrees with the third longitudinal axis. In some implementations, the fourth longitudinal axis forms an angle of 45 degrees with the third longitudinal axis. In some implementations, the fourth longitudinal axis forms an angle of 55 degrees with the third longitudinal axis. In some implementations, the fourth longitudinal axis forms an angle of 65 degrees with the third longitudinal axis. The second leg strap channel 616 may have an opening to receive the leg strap 300. The second leg strap channel 616 may have an opening to receive the attachment portion 119 of the leg strap 300.

Still referring to FIG. 6, the third leg strap channel 618 may extend along a fifth longitudinal axis, the fifth longitudinal axis forming an angle less than 90 degrees with the fourth longitudinal axis. In some implementations, the fifth longitudinal axis forms an angle of 25 degrees with the fourth longitudinal axis. In some implementations, the fifth longitudinal axis forms an angle of 35 degrees with the fourth longitudinal axis. In some implementations, the fifth longitudinal axis forms an angle of 45 degrees with the fourth longitudinal axis. In some implementations, the fifth longitudinal axis forms an angle of 55 degrees with the fourth longitudinal axis. In some implementations, the fifth longitudinal axis forms an angle of 65 degrees with the fourth longitudinal axis. The third leg strap channel 618 may have an opening to receive the leg strap 300. The third leg strap channel 618 may have an opening to receive the attachment portion 119 of the leg strap 300. The third leg strap channel 618 may be wider than the first leg strap channel 614. The third leg strap channel 618 may be parallel to the first leg strap channel 614.

Figure 7A:
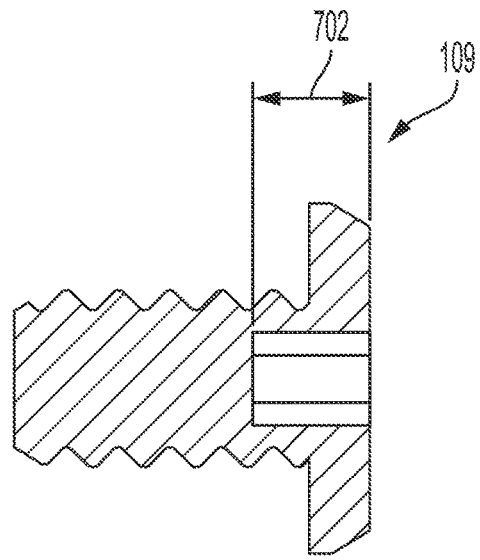
FIG. 7A illustrates a cross sectional view of the compression device fastener.

Referring now to FIG. 7A, illustrated is a cross sectional view of the compression device fastener 109. The compression device fastener 109 may be manufactured out of stainless steel. The compression device fastener 109 may have a minimum tensile strength of 30,000 PSI. The compression device fastener 109 may include a black oxide finish. The compression device fastener 109 top depth tolerance 702 may be 0.06 millimeters (mm).

Figure 7B:
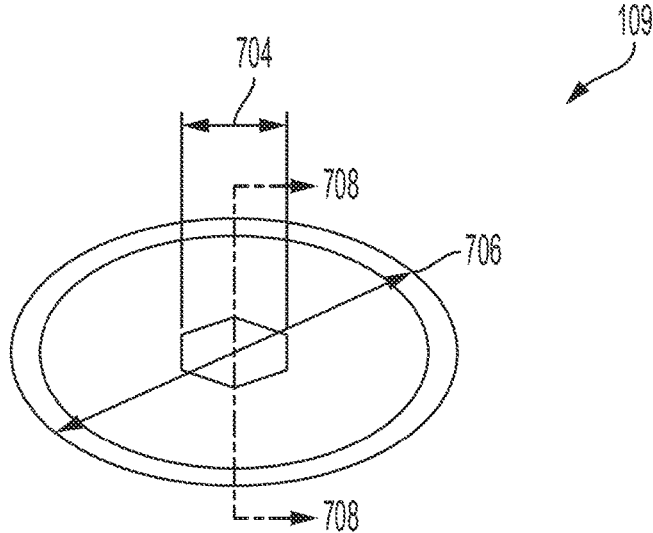
FIG. 7B illustrates a top view of the compression device fastener.

Referring now to FIG. 7B, illustrated is a top view of the compression device fastener 109. The compression device fastener 109 top may have a circular shape. The compression device fastener 109 may have a hexagonal shape 708. The hexagon height 704 may be 1.847 mm with a 0.073 mm tolerance. The compression device fastener 109 top may have a compression device fastener top diameter 706 of 7.938 mm with a tolerance of 0.313 mm.

Figure 7C:
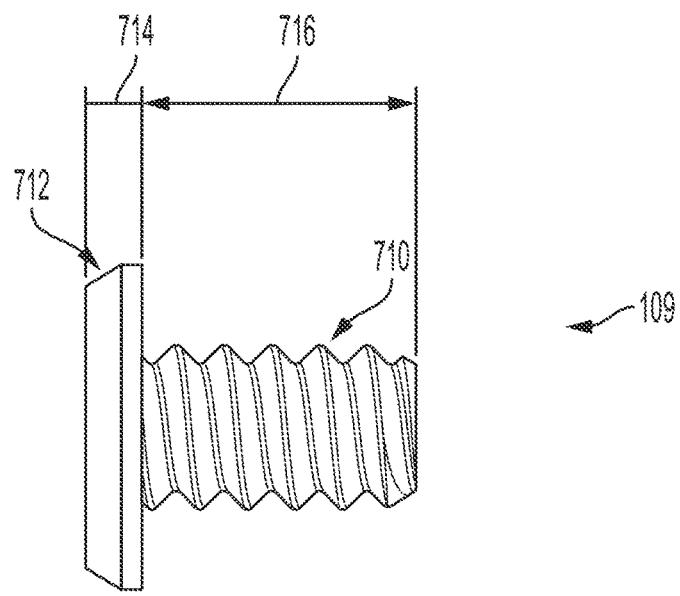
FIG. 7C illustrates a side view of the compression device fastener.

Referring now to FIG. 7C, illustrated is a side view of the compression device fastener 109. The compression device fastener thread 710 may be an M4×0.7 mm thread. The compression device fastener edge 712 may be 0.2 mm and angled at 45 degrees. The compression device top width 714 may be 0.813 mm with a 0.032 mm tolerance. The compression device fastener thread length 716 may have a length of 4 mm with a tolerance of 0.16 mm.

Figure 8A:
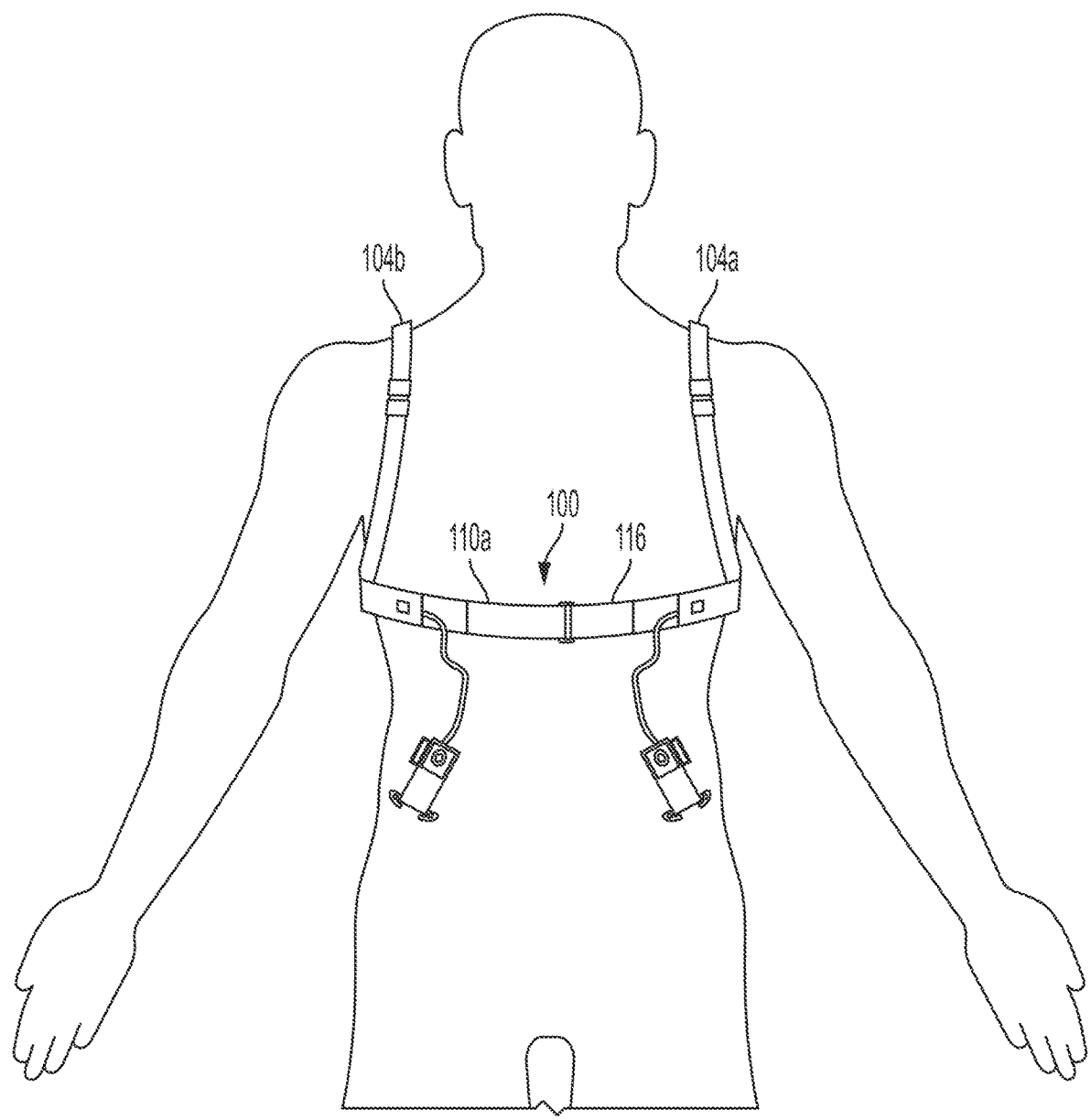
FIG. 8A illustrates the system worn by a user.

Referring now to FIG. 8A, and in brief overview, illustrated is the system 100 worn by a user. In some implementations, the system 100 is sized according to the size of the wearer. In other implementations, the system 100 may be manufactured in specific sizes (e.g., small, medium, and large). The system 100 may include one or more buckles and fasteners, such as a snap-fit buckle, that enables to wearer to adjust the fit of the system 100 and that may also facilitate the wearer in putting on the harness. For example, rather than sliding the upper extremities through the loops created by arm strap 104a and arm strap 104b, the chest strap 116 may couple with the chest strap fastener 110a. The chest strap 116 may couple with the chest strap fastener 110a via snap-fit buckles that enable to wearer to connect the system 100 at the front of the waist.

Figure 8B:
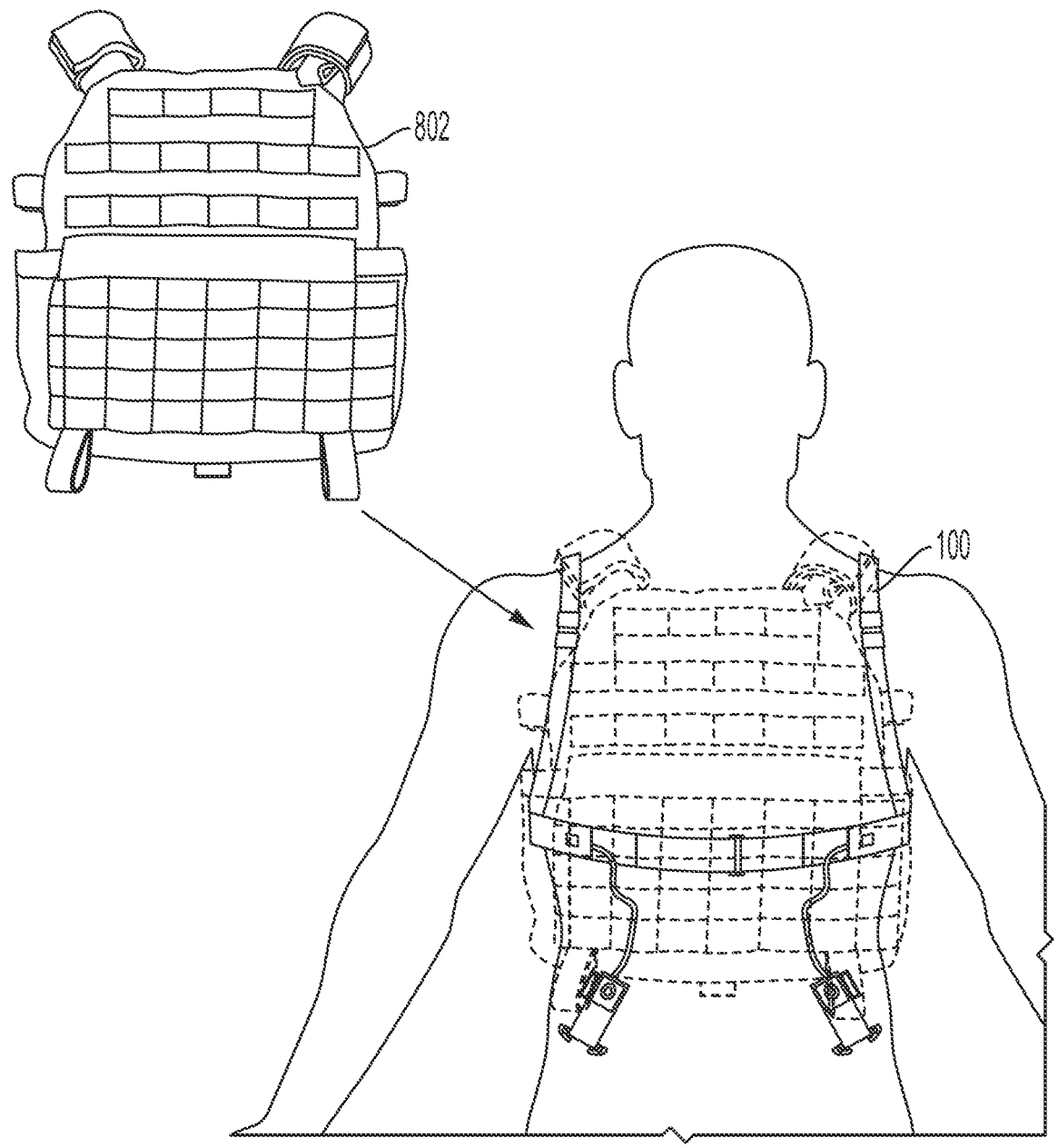
FIG. 8B illustrates the system worn underneath a vest.

Referring now to FIG. 8B, and in brief overview, illustrated is the system 100 worn underneath a vest 802. The system 100 may be worn by a soldier as part of the everyday combat dress. If the solider is injured and requires a tourniquet, the compression device (not pictured) may be coupled to the system 100 and used to apply pressure to the soldier's wounds or injured blood vessels. Wearing the system 100 prior to the need for a tourniquet may reduce the total amount of time required to stop (or reduce) blood flow to an injury because the soldier is already wearing the system 100 and a constriction mechanism (e.g., a strap or cuff) does not also need to be applied to the soldier.

Figure 8C:
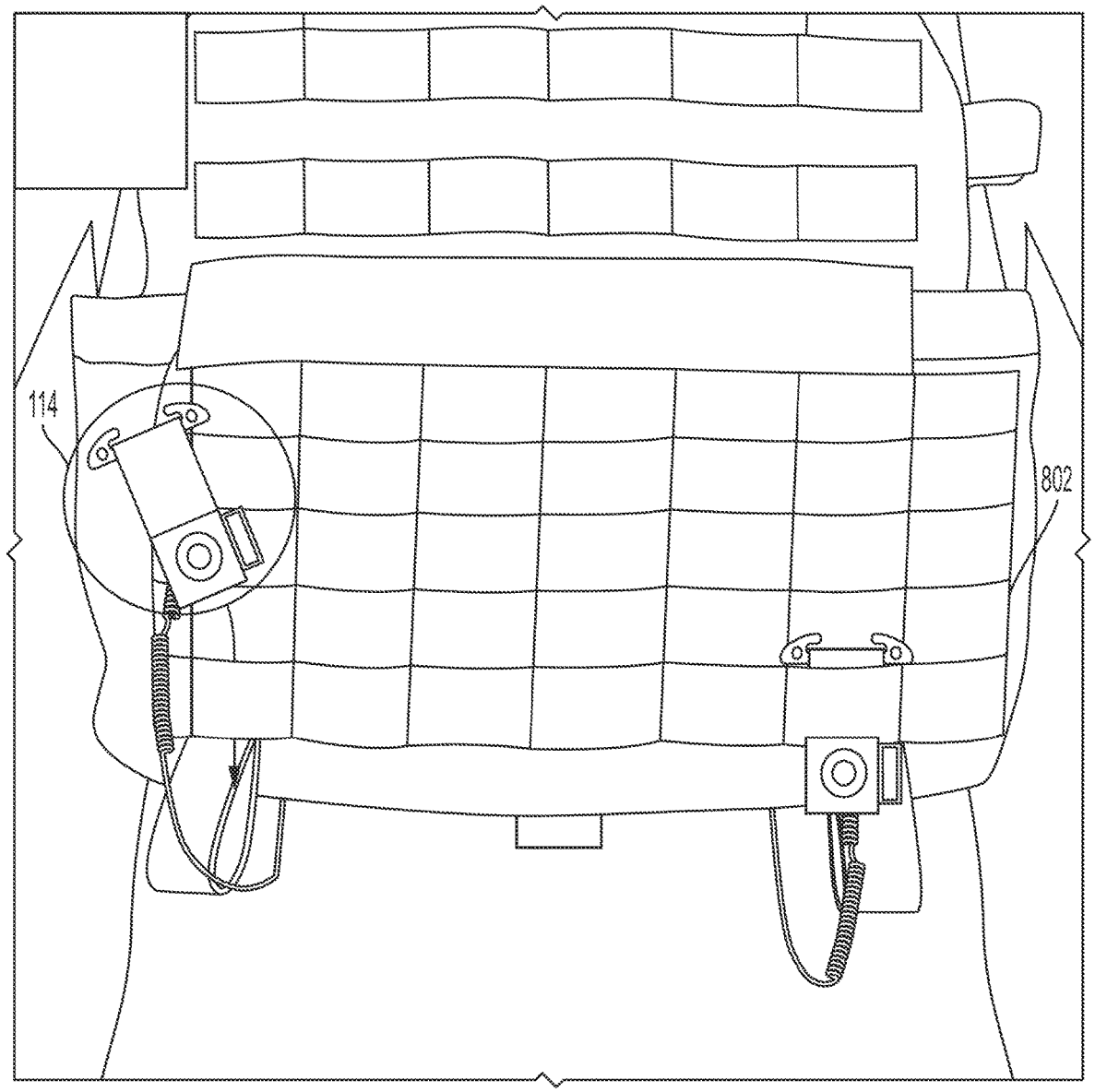
FIG. 8C illustrates the mount coupling to the vest.

Referring now to FIG. 8C, and in brief overview, illustrated is the mount 114 coupling to the vest 802. The mount 114 or the vest mount 402 may couple to the vest 802. The vest 802 may include modular lightweight load-carrying equipment (MOLLE) loops to facilitate the coupling of the mount 114 or the vest mount 402 with the vest 802.

Figure 8D:
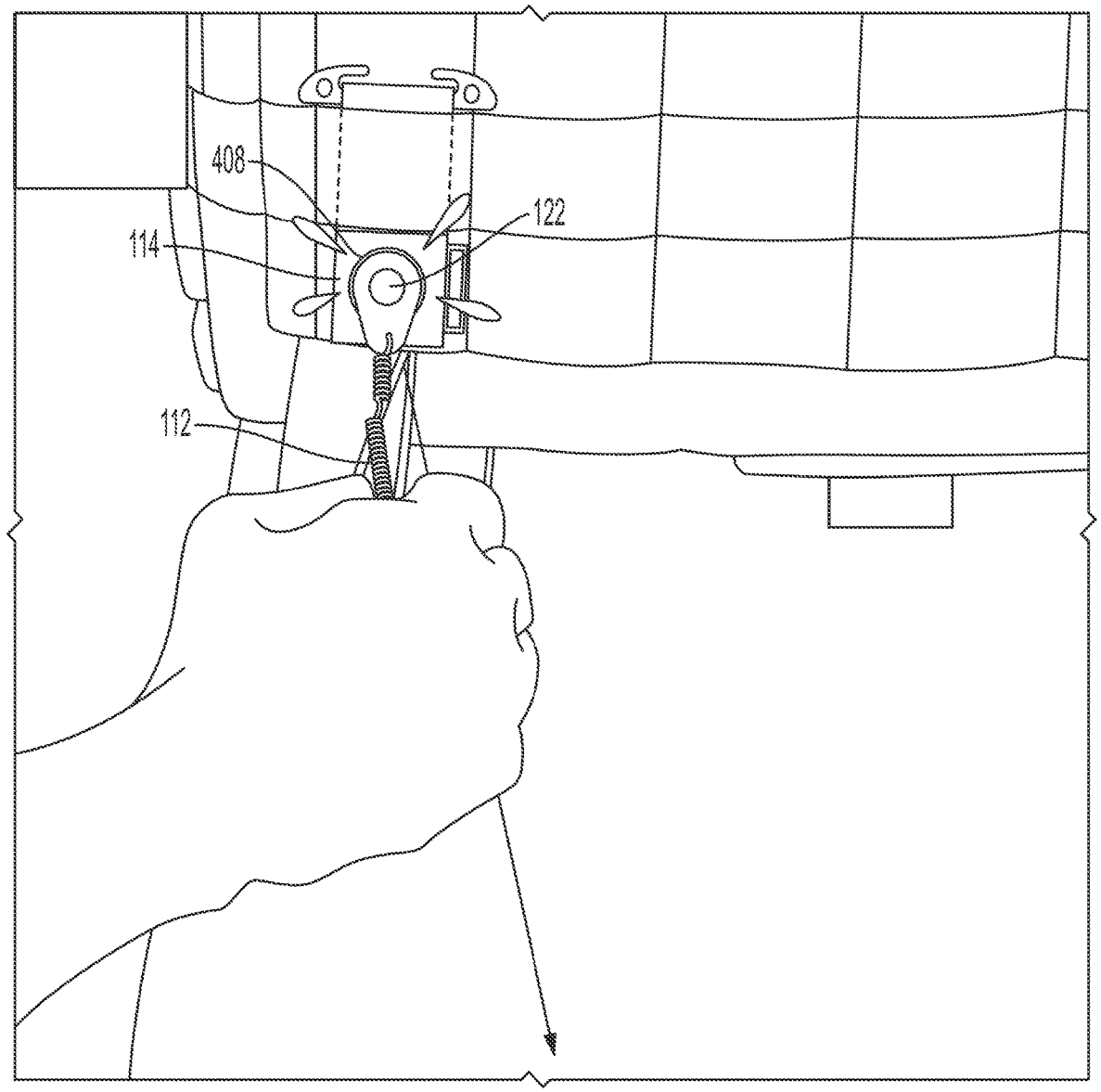
FIG. 8D illustrates an enlarged view of the user pulling the coil to disconnect the coil from the mount.

Referring now to FIG. 8D, illustrated is an enlarged view of the user pulling the coil 112 to disconnect the coil 112 from the mount 114. The coil 112 may disconnect from the mount 114 when the coil fastener 122 disconnects from the mount fastener 408.

Figure 8E:
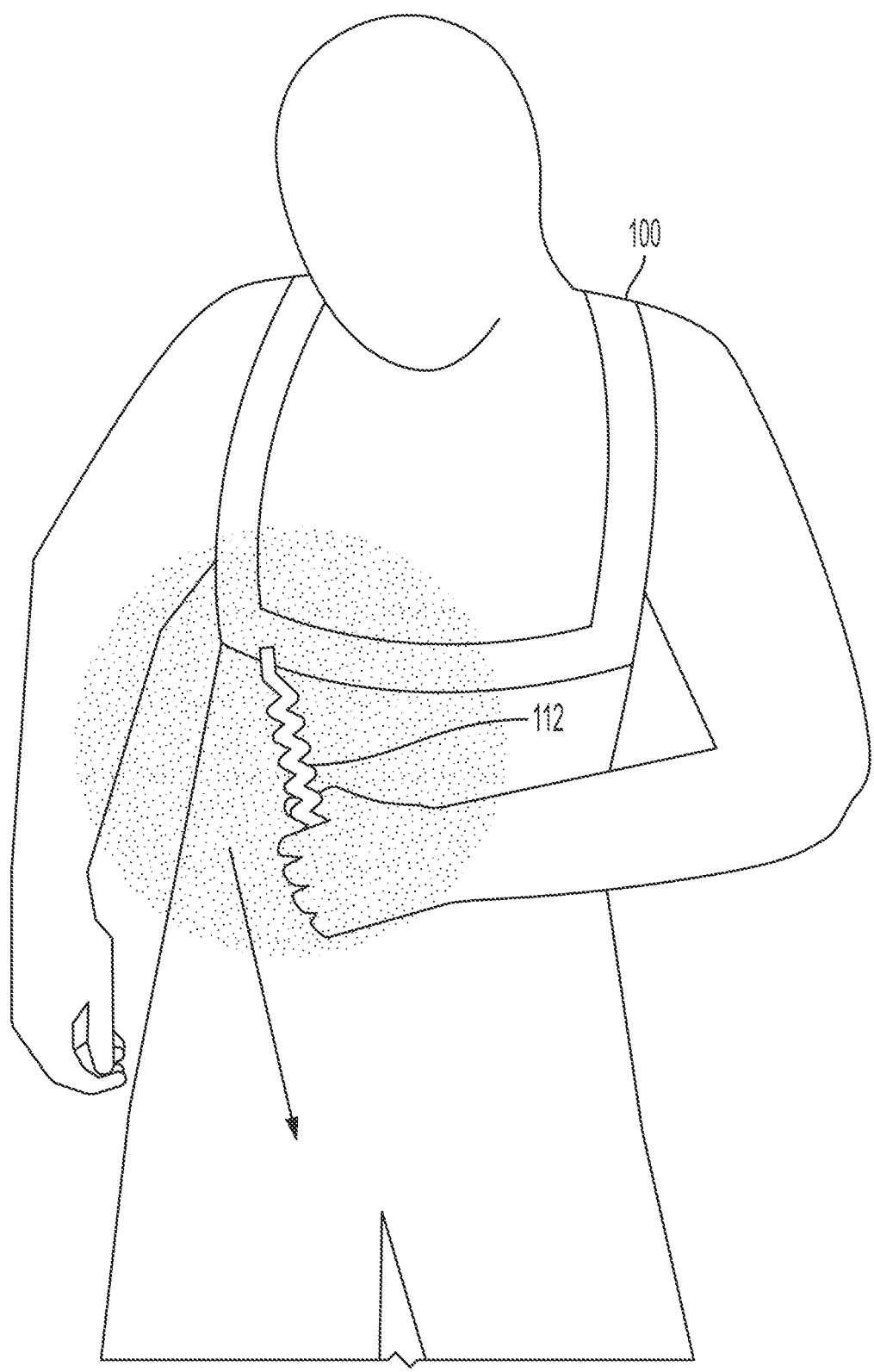
FIG. 8E illustrates the user pulling the coil to release the leg strap.

Referring now to FIG. 8E, illustrated is the user pulling the coil 112 to release the leg strap 300. If the coil 112 is not attached to the mount 114, then the leg strap 300 may pull out.

Figure 8F:
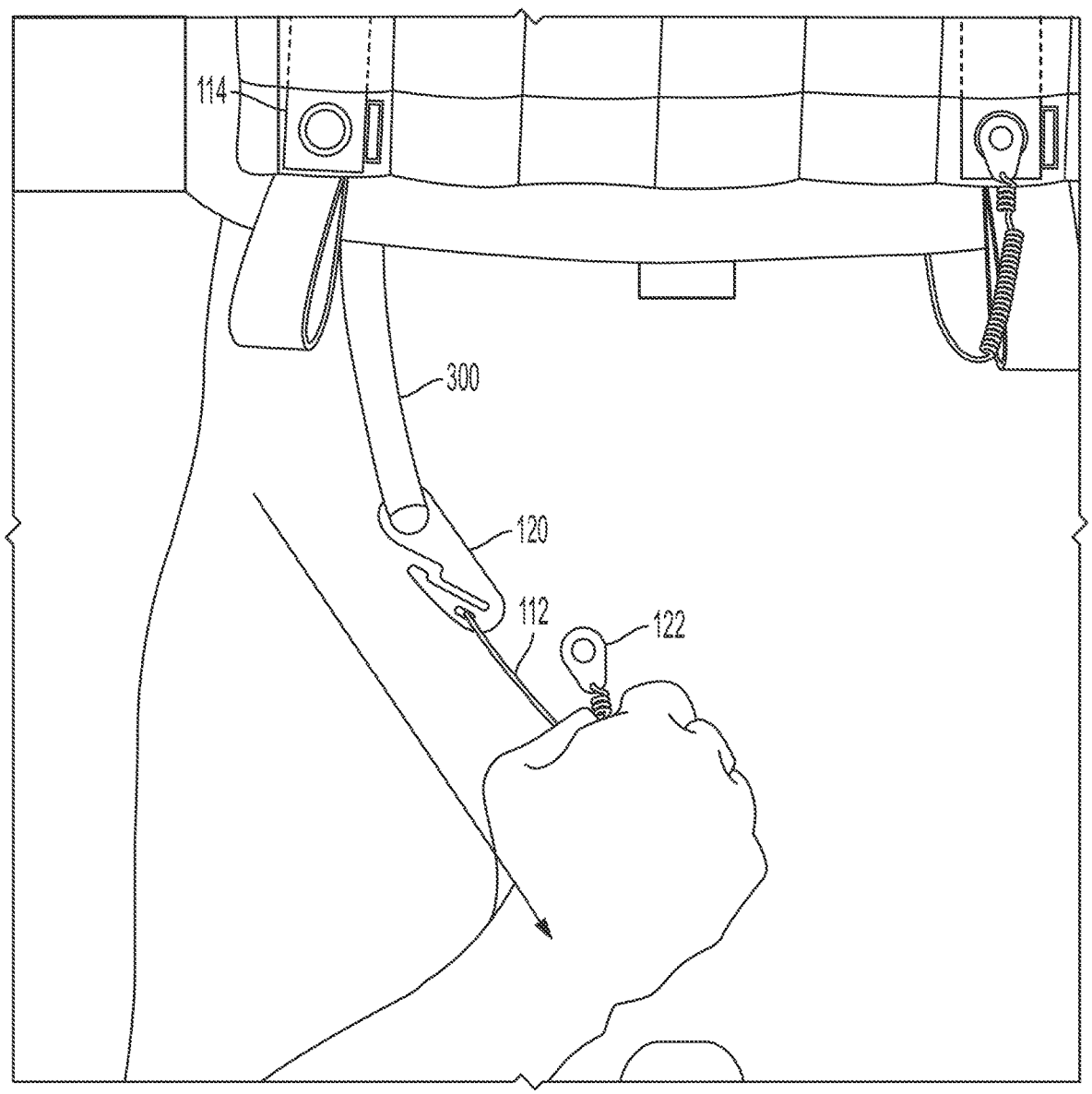
FIG. 8F illustrates an enlarged view of the user withdrawing the leg strap by pulling the coil.

Referring now to FIG. 8F, illustrated is an enlarged view of the user withdrawing the leg strap 300 by pulling the coil 112.

Figures 8G, 8H:
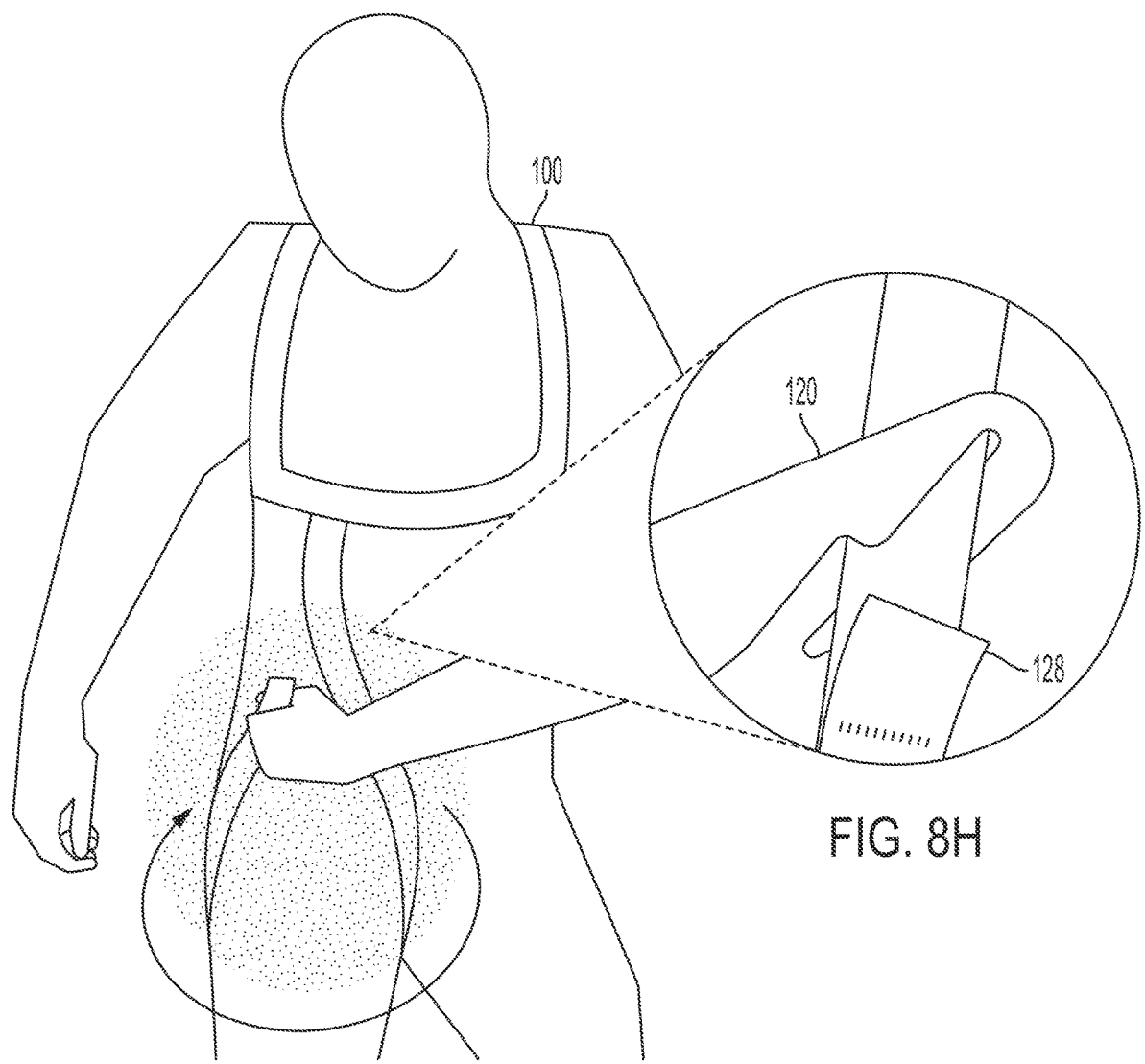
FIG. 8G illustrates the user securing the leg strap around the leg by attaching the hook to the leg strap.
FIG. 8H, illustrated is an enlarged view of the hook approaching the hook fastener.

Referring now to FIG. 8G, illustrated is the user securing the leg strap 300 around the lower junction point by attaching the hook 120 to the leg strap 300.

Referring now to FIG. 8H, illustrated is an enlarged view of the hook 120 approaching the hook fastener 128.

Figure 8I:
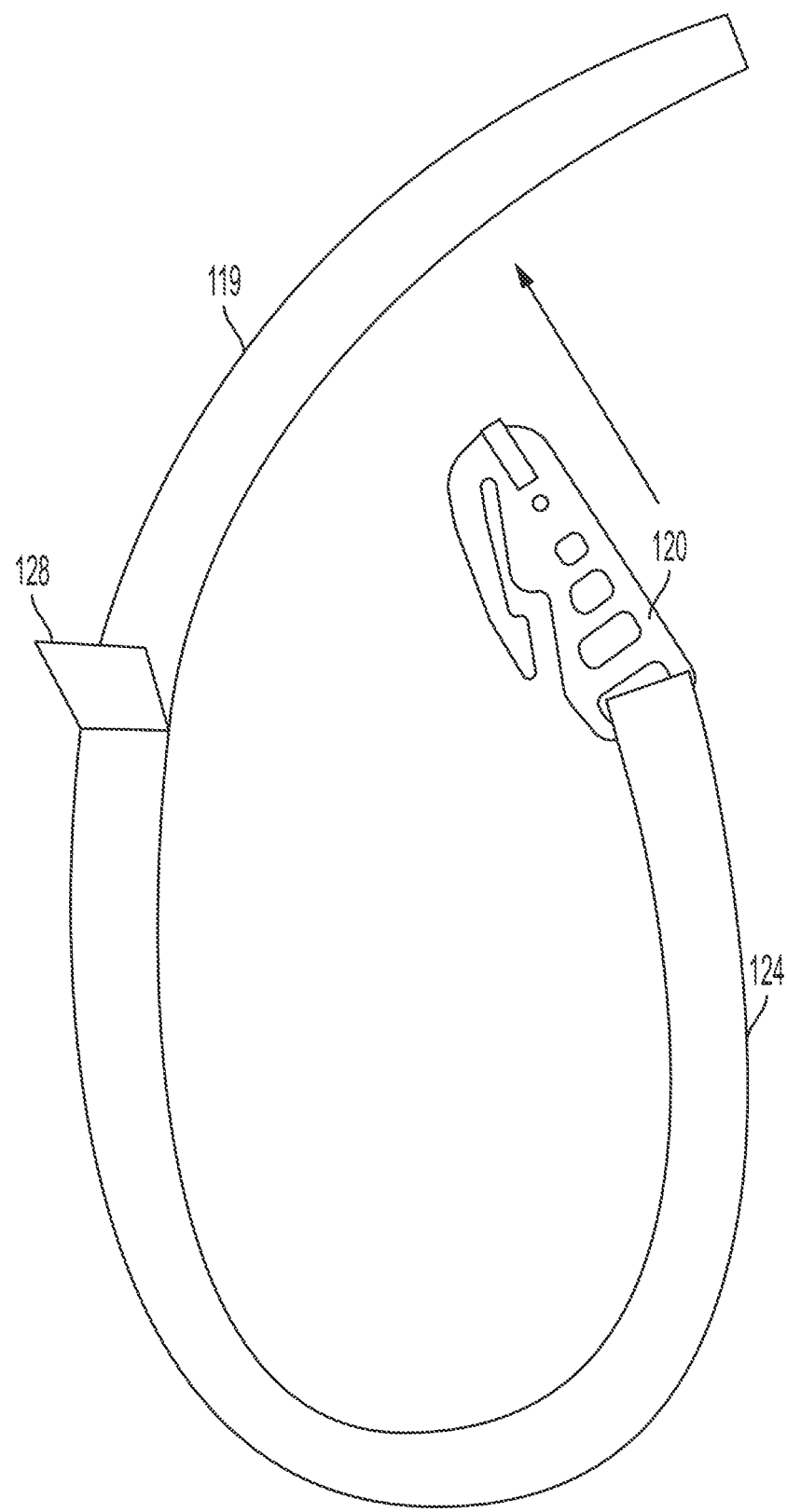
FIG. 8I illustrates the hook approaching attachment portion of the leg strap.

Referring now to FIG. 8I, illustrated is the hook 120 approaching the attachment portion 119 of the leg strap 300.

Figure 8J:
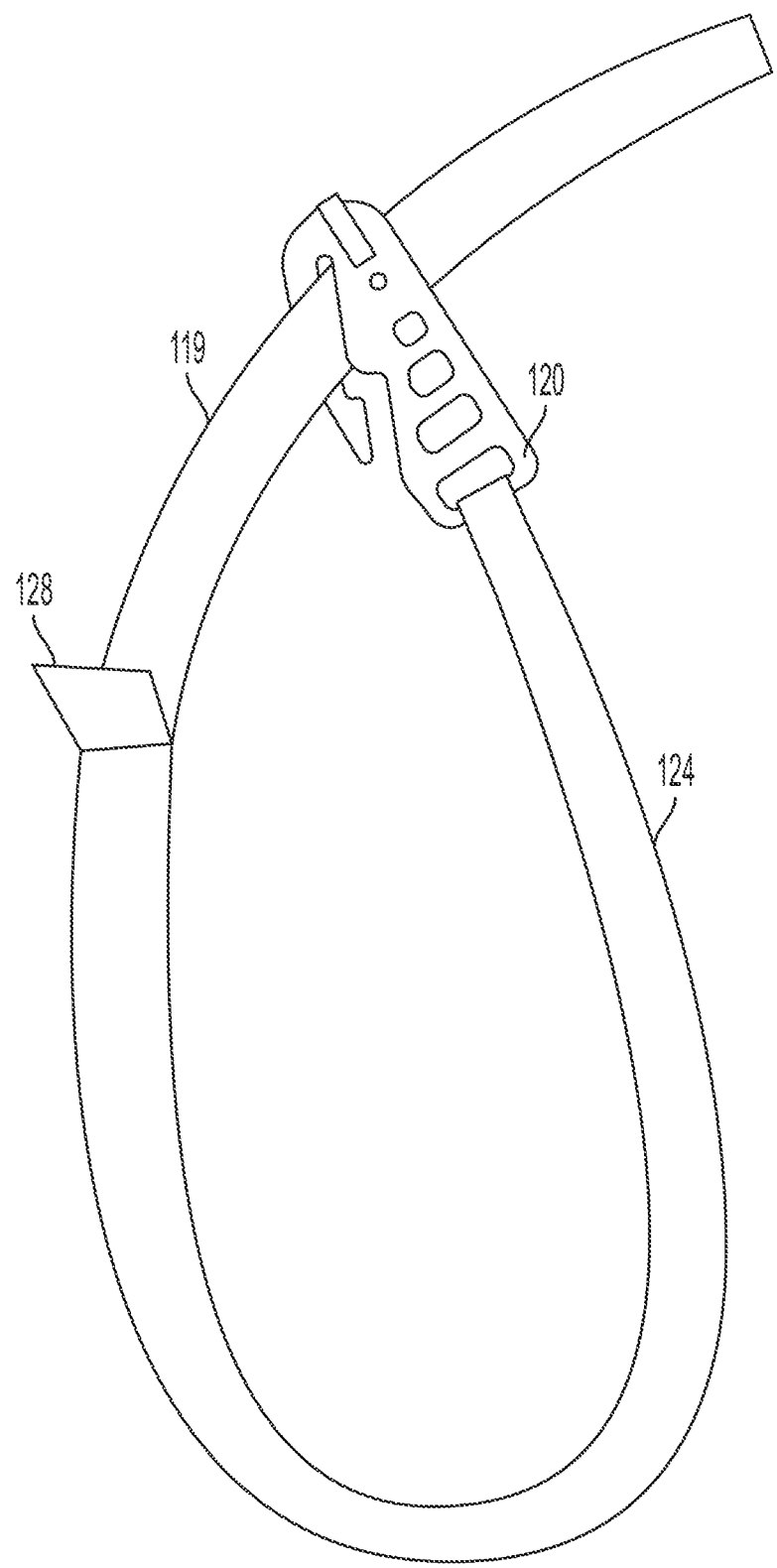
FIG. 8J illustrates the hook coupled to the attachment portion of the leg strap.

Referring now to FIG. 8J, illustrated is the hook 120 coupled to the attachment portion 119 of the leg strap 300.

Figure 8K:
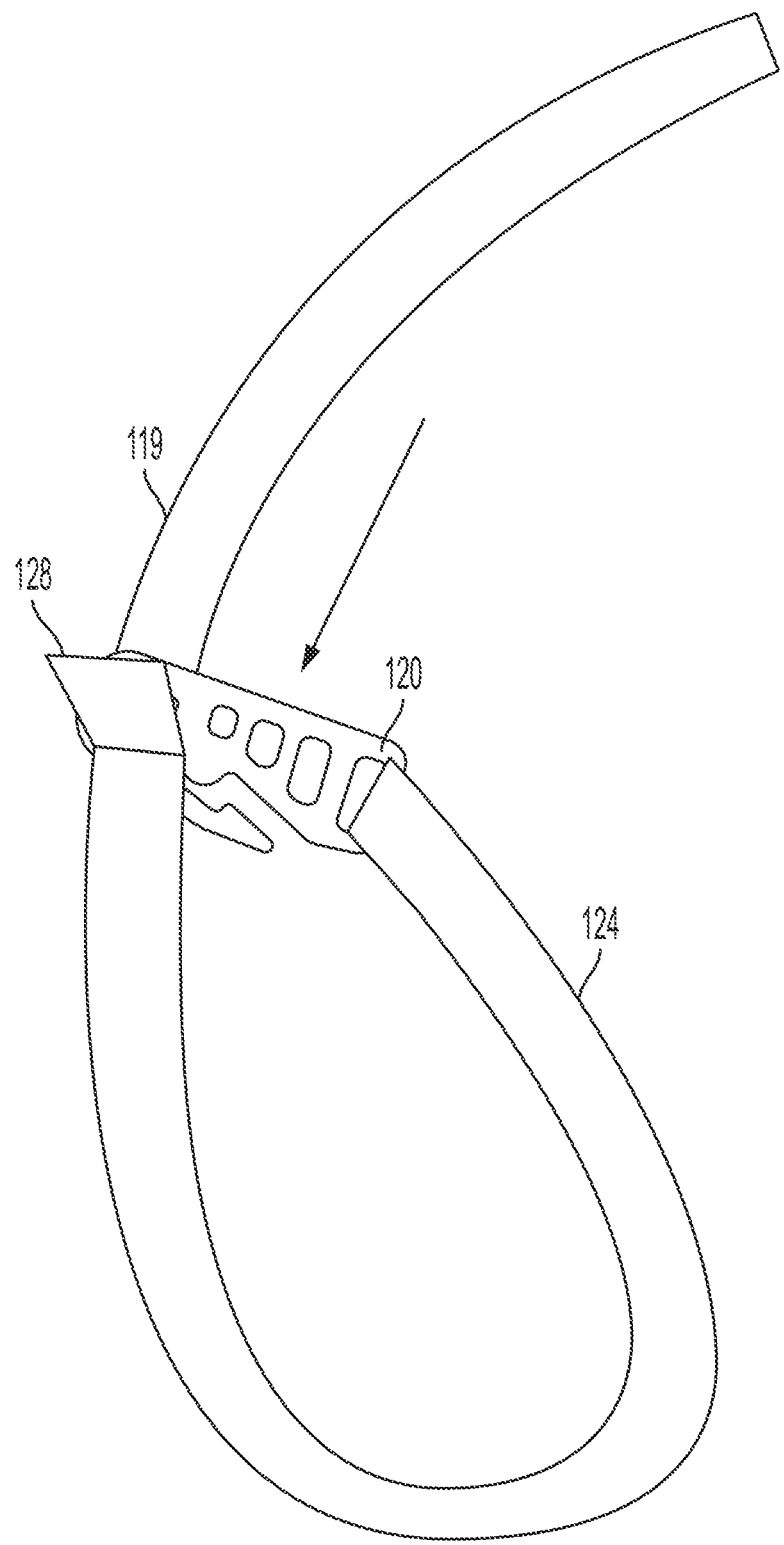
FIG. 8K illustrates the hook secured to the leg strap.

Referring now to FIG. 8K, illustrated is the hook 120 secured to the attachment portion 119 of the leg strap 300. The simple operation of the system 100 may enable the system 100 to be operated in high stress environment with low motor skills.

Figure 8L:
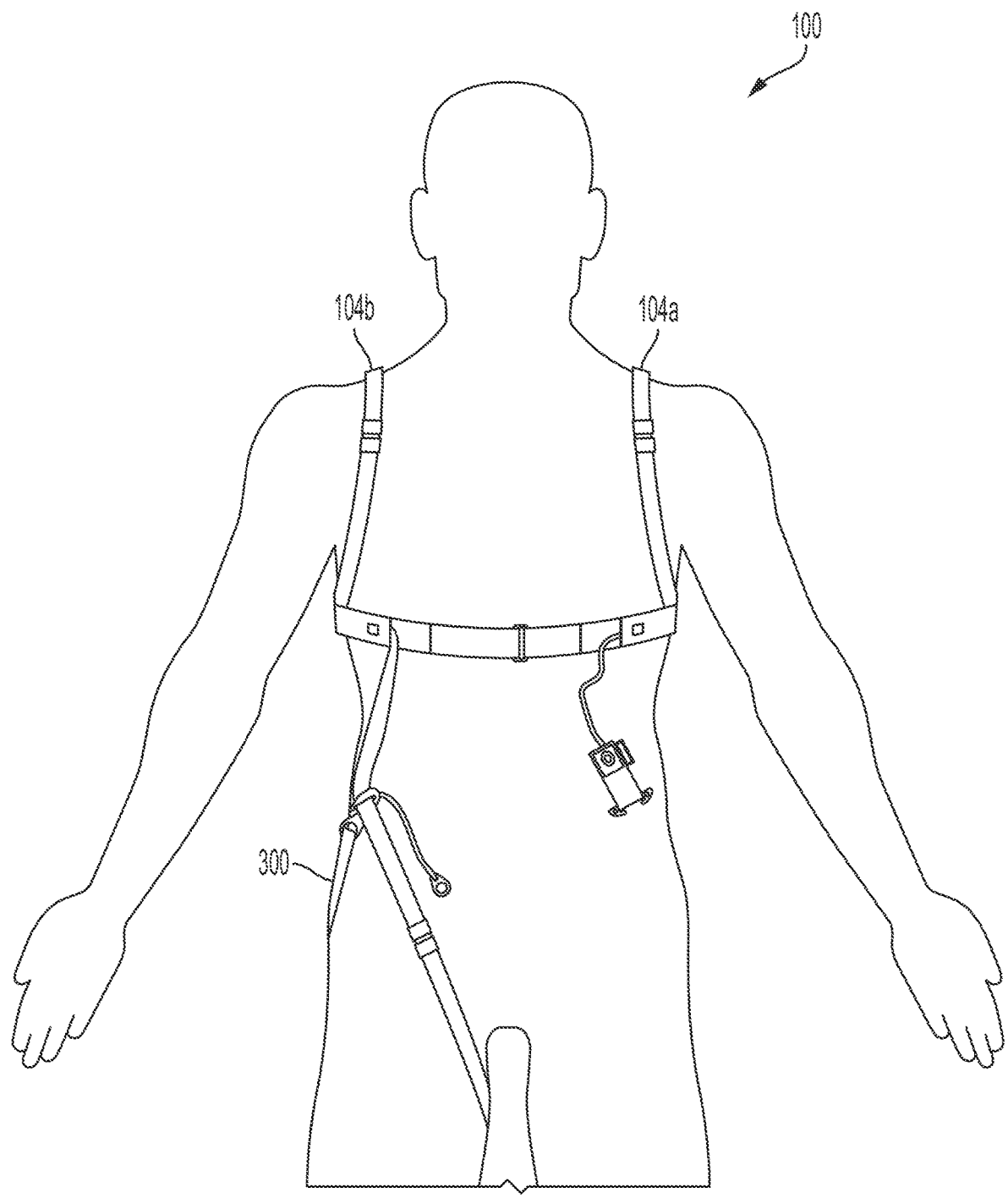
FIG. 8L the leg strap secured around the leg.

Referring now to FIG. 8L, and in brief overview, illustrated is the leg strap 300 secured around the leg. The constriction of the leg strap 300 or arm strap 104 with the compression device may cause the depression of the compression device into the wearer's upper junctional area or lower junctional area.

Still referring to FIG. 8L, and in further detail, in some implementations, the leg strap 300 may be secured around an arm or another bodily junction point. The compression device may constrict the arm strap 104 or the leg strap 300 to provide a compressive force to the location. In some implementations, the location is an arterial location or the junctional area. The compression device applies pressure to a specific arterial location. The pressure is achieved by the constriction of the arm strap 104 or the leg strap 300 and the form of the compression device pressing into the body. For example, the compression device may be coupled with the arm strap 104 or the leg strap 300 over a specific arterial location to provide a compressive force to the arterial location as the compression device constricts the webbing. In some implementations, all or part of the system 100 may be applied to wearer after the injury. For example, the system 100 be worn around the waist and shoulders of a wearer and the leg strap 300 of the device may be deployed after the injury. The system 100 may be worn and encircle (partially or totally) at least one upper junctional area and at least one lower junctional area. In some implementations, the system 100 may only encircle one or more upper junctional areas or one or more lower junctional areas.

The disclosed system and methods may be embodied in other specific forms without departing from the spirit or essential characteristics thereof. The forgoing implementations are therefore to be considered in all respects illustrative, rather than limiting of the invention.

What is claimed is:

1. A system for an attachment mechanism for attaching a strap around a body extremity comprising:
    a hook having a first longitudinal axis and coupled to the strap at a first region of the hook;
    a first channel allowing the attachment mechanism to receive the strap;
    a second channel extending from the first channel and having an opening allowing the attachment mechanism to secure the strap, the opening extending along a second longitudinal axis, the second longitudinal axis forming an angle of less than ninety degrees with the first longitudinal axis;
    a cord attached at a third region of the hook;
    a fastener attached to the cord; and
    a Modular Lightweight Load-Carrying Equipment (MOLLE) T mount engaged to the fastener.

2. The system of claim 1, wherein the angle formed by the second longitudinal axis is less than twenty degrees with the first longitudinal axis.

3. The system of claim 1, further comprising a third channel between the first channel and the second channel, the third channel having a first slit with a first area for gripping the strap.

4. The system of claim 3, wherein the third channel includes a second slit with a second area and a third slit with a third area, wherein the third area is less than the second area, wherein the second area is less than the first area.

5. The system of claim 1, wherein the strap comprises:
    a first portion;
    an attachment portion attached to the first portion;
    a main portion attached to the attachment portion; and
    an elastic portion attached to the main portion.

6. The system of claim 5, wherein the strap further comprises a hook-fastener disposed between the attachment portion and the main portion.

7. The system of claim 6, wherein the first channel is capable of receiving the hook-fastener of the strap.

8. The system of claim 5, wherein the main portion includes a rivet for receiving a pressure ratchet.

9. The system of claim 5, wherein the attachment portion has a first elasticity.

10. The system of claim 5, wherein the elastic portion has a second elasticity.

11. A method for attaching a strap around a body extremity for controlling blow flow comprising:
    providing an apparatus comprising:
        a hook having a first longitudinal axis and coupled to the strap at a first region of the hook;

a first channel to receive the strap;
a second channel extending from the first channel and having an opening to secure the strap, the opening extending along a second longitudinal axis, the second longitudinal axis forming an angle of less than ninety degrees with the first longitudinal axis;
a cord attached to a third region of the hook;
a fastener attached to the cord; and
a mount engaged to the fastener;

wrapping the strap around a junction;

receiving, by the second channel, the strap to secure the strap around the junction;

disconnecting the fastener from the mount responsive to wrapping the strap around the junction; and extending the cord responsive to wrapping the strap around the junction.

\* \* \* \* \*